United States Patent
Claus et al.

(10) Patent No.: US 10,206,645 B2
(45) Date of Patent: Feb. 19, 2019

(54) MULTI-PERSPECTIVE INTERVENTIONAL IMAGING USING A SINGLE IMAGING SYSTEM

(71) Applicant: General Electric Company, Schenectady, NY (US)

(72) Inventors: Bernhard Erich Hermann Claus, Niskayuna, NY (US); David Allen Langan, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/857,969

(22) Filed: Sep. 18, 2015

(65) Prior Publication Data
US 2017/0079607 A1 Mar. 23, 2017

(51) Int. Cl.
G06K 9/00 (2006.01)
A61B 6/00 (2006.01)
A61B 6/02 (2006.01)

(52) U.S. Cl.
CPC ............ *A61B 6/5211* (2013.01); *A61B 6/025* (2013.01); *A61B 6/461* (2013.01)

(58) Field of Classification Search
None
See application file for complete search history.

(56) References Cited

U.S. PATENT DOCUMENTS

| | | | | |
|---|---|---|---|---|
| 6,577,889 B2* | 6/2003 | Ichihashi | ............. | A61B 6/4233 378/63 |
| 6,628,977 B2* | 9/2003 | Graumann | ............... | A61B 6/12 600/407 |
| 6,813,512 B2* | 11/2004 | Aldefeld | ................ | A61B 5/055 600/410 |
| 8,027,714 B2 | 9/2011 | Shachar | | |

(Continued)

OTHER PUBLICATIONS

Speidel MA1, Tomkowiak MT, Raval AN, Van Lysel MS, Three-dimensional tracking of cardiac catheters using an inverse geometry x-ray fluoroscopy system, Med Phys. Dec. 2010;37(12):6377-89.*

(Continued)

*Primary Examiner* — Andrae S Allison
(74) *Attorney, Agent, or Firm* — GE Global Patent Operation; Seema Katragadda

(57) ABSTRACT

A method for imaging a target region in a subject is presented. The method includes selecting one or more tomographic angle sequences, acquiring one or more image sequences corresponding to the one or more tomographic angle sequences, where each image sequence has a corresponding tomographic angle sequence, deriving geometric information corresponding to one or more structures of interest in at least one of the image sequences, identifying visualization information, generating one or more displacement maps based on the geometric information, the visualization information, at least a subset of at least one of the one or more tomographic angle sequences, or combinations thereof, transforming at least a subset of images in the one (Continued)

or more image sequences based on corresponding displacement maps to create one or more transformed/stabilized image sequences, and visualizing on a display the one or more transformed/stabilized image sequences to provide a stabilized presentation of the target region.

22 Claims, 7 Drawing Sheets

(56) References Cited

U.S. PATENT DOCUMENTS

| | | | |
|---|---|---|---|
| 8,233,962 B2* | 7/2012 | Kukuk | A61B 6/481 378/62 |
| 8,532,742 B2 | 9/2013 | Unal et al. | |
| 2002/0190988 A1* | 12/2002 | Maillot | G06T 17/20 345/428 |
| 2004/0196285 A1* | 10/2004 | Rice | G06T 17/20 345/423 |
| 2005/0256398 A1 | 11/2005 | Hastings et al. | |
| 2007/0110298 A1* | 5/2007 | Graepel | G06K 9/00355 382/154 |
| 2007/0216680 A1* | 9/2007 | Wang | G06T 15/04 345/424 |
| 2007/0276216 A1* | 11/2007 | Beyar | A61B 6/12 600/407 |
| 2008/0095468 A1* | 4/2008 | Klemmer | H04N 9/3194 382/285 |
| 2008/0144902 A1* | 6/2008 | Radulescu | G06T 7/2026 382/130 |
| 2013/0172726 A9 | 7/2013 | Saadat et al. | |
| 2013/0282005 A1 | 10/2013 | Koch et al. | |
| 2016/0029987 A1* | 2/2016 | Langan | A61B 6/486 378/8 |

OTHER PUBLICATIONS

Chou et al, 2D/3D image registration using regression learning, Computer Vision and Image Understanding 117 (2013) 1095-1106.*

Brost Al, Liao R, Strobel N, Hornegger J., Respiratory motion compensation by model-based catheter tracking during EP procedures, Med Image Anal. Oct. 2010;14(5):695-706. doi: 10.1016/j.media.2010.05.006. Epub Jun. 10, 2010.*

Xie, Yaoqin, et al. "Feature-based rectal contour propagation from planning CT to cone beam CT." Medical physics 35.10 (2008): 4450-4459.*

Brost, et al., "Respiratory Motion Compensation by Model-Based Catheter Tracking during EP Procedures", Med Image Anal., vol. 14, Issue 5, pp. 695-706, 2010.

Schenderlein et al., "Three-Dimensional Catheter Tip Tracking from Asynchronous Biplane X-Ray Image Sequencesusing Non-Linear State Filtering", pp. 234-238, 2011.

Khan et al., "Amigo,™ a Novel Remote Catheter System, Demonstrates Safety and Efficacy", 2012, 1 page.

Bourier et al., "Navigation for fluoroscopy-guided cryo-balloon ablation procedures of atrial fibrillation", Medical Imaging, Feb. 2012, 8 Pages.

* cited by examiner

MULTI-PERSPECTIVE INTERVENTIONAL IMAGING USING A SINGLE IMAGING SYSTEM

BACKGROUND

Embodiments of the present specification relate to imaging, and more particularly to a system and method for multi-perspective imaging via use of a single plane interventional imaging system.

Minimally invasive medical procedures are becoming increasingly important due to their success in improving patient outcome and minimizing cost. Consequently, increasingly complex interventions are being performed thereby necessitating imaging systems to provide expanded and additional functionality in order to support these complex interventions. These interventional procedures may include catheter-based techniques and/or needle-based techniques. The catheter-based interventional techniques entail navigating a catheter through vasculature of the patient to reach a target region such as a diseased region. In the needle-based techniques, a needle is guided through the anatomy to reach a target region. The needle-based techniques are typically used to deliver therapy to a cancerous lesion and/or the spine (for example, vertebroplasty), or to biopsy tissues.

Presently, several imaging modalities such as X-ray fluoroscopy, X-ray computed tomography (CT), and/or cone beam computed tomography (CBCT) imaging systems are used to acquire image data corresponding to an object of interest such as the patient. Furthermore, bi-plane systems or CBCT imaging systems are used to gain information that goes beyond two-dimensional (2D) information (for example, three-dimensional (3D) information) and hence reduce ambiguity. Generally, CBCT imaging entails 3D imaging with data acquired using a so-called spin acquisition with a C-arm system, where the gantry is rotated ~200 degrees about the patient to acquire projection data that is used to generate a 3D volume. However, the gantry rotation is workflow intrusive and often prohibitive due to the proximity of auxiliary equipment such as an anesthesiology cart, an ultrasound imaging system, lines to the patient, and the like. Furthermore, workflow is also hampered by patient positioning due to radial access and/or off-center anatomy/region of interest (ROI). Also, a spin is generally constrained to a single or very few limited time points. Consequently, temporal information that is desirable for catheter guidance or observing bolus dynamics, for example, may not be available. Moreover, CBCT imaging is further complicated as CBCT imaging needs to be synchronized with the contrast agent injection and/or breath hold of the patient, in order to avoid a loss in image quality, for example due to patient motion.

Certain currently available techniques for navigating the catheter through complex vasculature entail use of a single 2D viewing plane. By way of example, X-ray images acquired for a single view angle or gantry angle relative to the patient, are often combined with the injection of a contrast medium in order to visualize the vasculature. In order to view the imaged anatomy from a different angle, the gantry needs to be moved to a different angle, and a 2D sequence corresponding to that new gantry position may be acquired. However, navigating the catheter through complex vasculature employing the single 2D viewing plane is laborious and time consuming. Consequently, procedure time, radiation dose, as well as contrast medium dose are impacted.

Moreover, some presently available techniques call for use of bi-plane imaging systems. The bi-plane systems employ two imaging sub-systems, generally with each imaging sub-system residing on an independent gantry. Bi-plane imaging provides two concurrent views from different angulations/perspectives, thereby providing additional information that may help in visualizing the 3D structure of the imaged anatomy. However, the bi-plane system is very expensive in terms of equipment and required facility. Moreover, maneuvering the second imaging plane into position is workflow intrusive.

Procedure X-ray dose, contrast dose, and procedure duration associated with the currently available techniques also negatively impact patient outcome and procedure cost. Other disadvantages of the presently available techniques also include exposure of clinical staff to radiation.

BRIEF DESCRIPTION

In accordance with aspects of the present specification, a method for imaging a target region in a subject is presented. The method includes selecting one or more tomographic angle sequences. Furthermore, the method includes acquiring one or more image sequences corresponding to the one or more tomographic angle sequences, where each of the one or more image sequences has a corresponding tomographic angle sequence. In addition, the method includes deriving geometric information corresponding to one or more structures of interest in at least one of the one or more image sequences. The method also includes identifying visualization information. Moreover, the method includes generating one or more displacement maps based on the geometric information, the visualization information, at least a subset of at least one of the one or more tomographic angle sequences, or combinations thereof. Additionally, the method includes transforming at least a subset of images in the one or more image sequences based on corresponding displacement maps to create one or more transformed/stabilized image sequences. Also, the method includes visualizing on a display the one or more transformed/stabilized image sequences to provide a stabilized presentation of the target region.

In accordance with another aspect of the present specification, a system is presented. The system includes a multi-perspective platform configured to select one or more tomographic angle sequences, acquire one or more image sequences corresponding to the one or more tomographic angle sequences, where each of the one or more image sequences has a corresponding tomographic angle sequence; derive geometric information corresponding to one or more structures of interest in at least one of the one or more image sequences, identify visualization information, generate one or more displacement maps based on the geometric information, the visualization information, at least a subset of at least one of the one or more tomographic angle sequences, or combinations thereof, transform at least a subset of images in the one or more image sequences based on corresponding displacement maps to create one or more transformed/stabilized image sequences, and visualize on a display the one or more transformed/stabilized image sequences to provide a stabilized presentation of the target region.

In accordance with yet another aspect of the present specification, a system for imaging is presented. The system includes an acquisition unit configured to obtain one or more image sequences corresponding to a target region in a subject. Moreover, the system includes a processing unit in operative association with the acquisition unit and comprising a multi-perspective imaging platform, where the multi-perspective imaging platform is configured to select one or more tomographic angle sequences, acquire one or more image sequences corresponding to the one or more tomographic angle sequences, where each of the one or more image sequences has a corresponding tomographic angle sequence; derive geometric information corresponding to one or more structures of interest in at least one of the one or more image sequences, identify visualization information, generate one or more displacement maps based on the geometric information, the visualization information, at least a subset of at least one of the one or more tomographic angle sequences, or combinations thereof, transform at least a subset of images in the one or more image sequences based on corresponding displacement maps to create one or more transformed/stabilized image sequences, and visualize on a display the one or more transformed/stabilized image sequences to provide a stabilized presentation of the target region.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
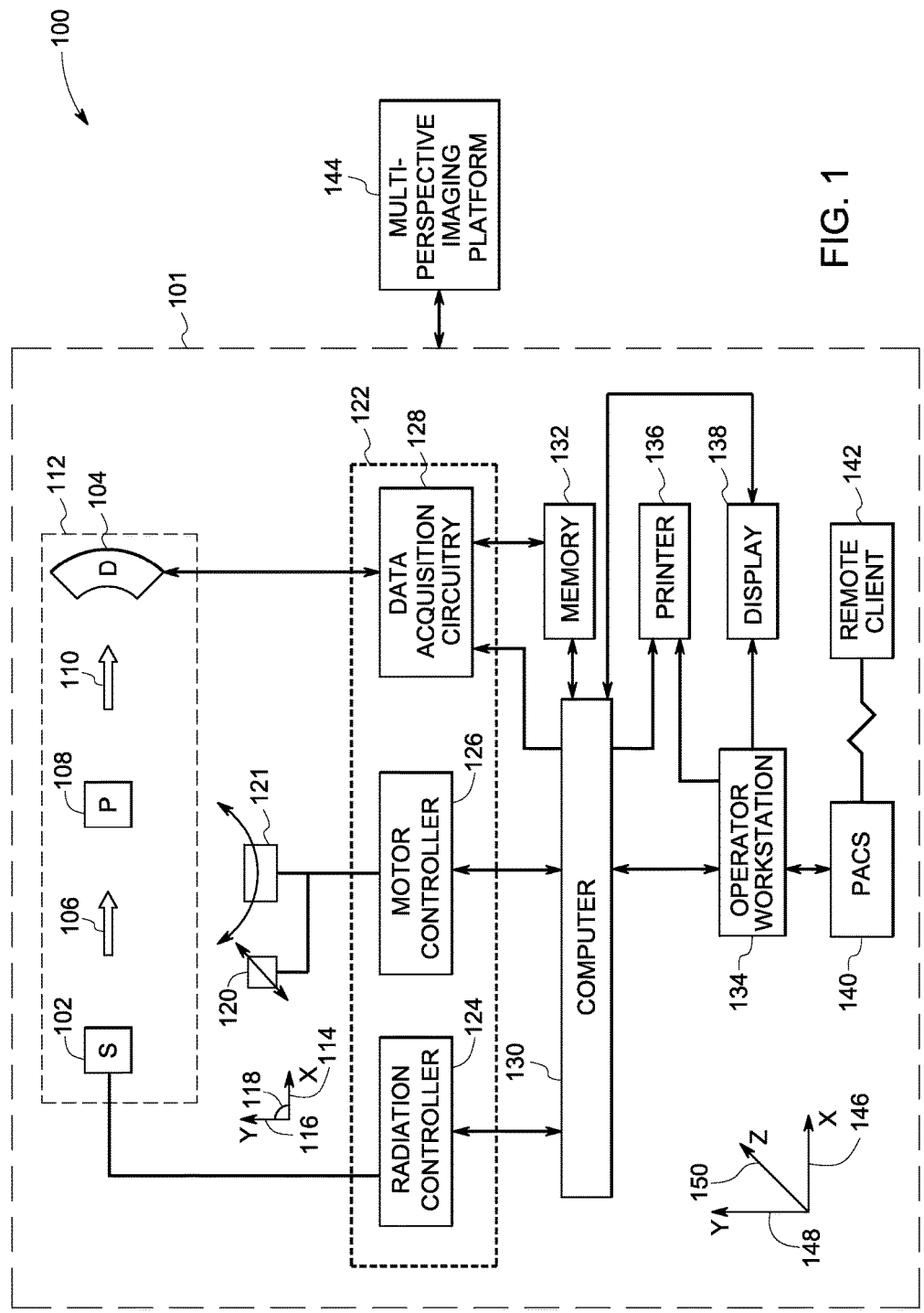
FIG. 1 is a diagrammatical representation of an exemplary single-plane imaging system configured to provide multi-perspective interventional imaging, in accordance with aspects of the present specification.

As will be described in detail hereinafter, systems and methods for multi-perspective imaging using a single imaging system, in accordance with aspects of the present specification, are presented. More particularly, the systems and methods are configured to generate one or more stabilized image sequences and present the stabilized image sequences to a user. Use of the exemplary systems and methods presented hereinafter provides enhanced visualization of structures within an imaged volume, thereby providing visualization support to the user for diagnosis and guidance support during interventional procedures.

In certain 3D imaging procedures including procedures using an interventional C-arm imaging system or similar systems, it may be desirable to visualize internal structures of a patient. Aspects of the present specification utilize a C-arm imaging system to provide such images. In particular, a C-arm imaging system may be operated in an exemplary tomosynthesis acquisition mode, where an X-ray detector and source (for example, an X-ray tube) may continuously orbit within respective planes above and below a patient support table. As will be appreciated, in such tomosynthesis acquisitions, an acquisition motion or trajectory having a small tomographic angle may be employed. Such acquisitions allow a user easy access to a patient, while circumventing collision hazards with procedure room apparatus, patient, and/or other medical staff, thereby overcoming shortcomings of the currently available techniques. As used herein, the term "tomosynthesis" is used to refer to an acquisition mode that may be used to reconstruct a volumetric tomosynthesis dataset. However, in certain embodiments a volumetric dataset may not be generated.

In certain embodiments, such an interventional imaging system may be used to acquire projection data corresponding to a determined range of projection angles. In particular, the acquisition procedure utilizes an X-ray source that may traverse a trajectory (or orbit) that is essentially located within a single plane on one side of the patient. It may be noted that without additional processing, the position and/or orientation of structures of interest that are visible in the acquired image sequence may continuously change within the image due to the gantry motion as a function of time, therefore making interpretation of the image sequence and image-based guidance extremely challenging. In accordance with aspects of the present specification, one or more sequences of projection images may be acquired and transformed/warped based on user-specified static perspectives or static view angles to generate one or more stabilized image sequences. It may be noted that the terms "perspective," "view angle," and "visualization view angle" may be used interchangeably. Also, it may be noted that in certain embodiments the term "view angle" may also refer to an acquisition view angle or a visualization view angle. The stabilized image sequences represent a view of the imaged structure as if the view angle is static relative to the imaged structure of interest, thereby enabling an improved presentation of the imaged 3D structures. In one embodiment two or more stabilized sequences, corresponding to two or more visualization view angles, may be presented to the user, thereby providing multi-perspective imaging.

To that end, geometric information corresponding to structures of interest within the images may be derived. The geometric information may include information regarding 2D locations of structures of interest in the projection images, 3D locations of structures of interest within the imaged volume, 2D locations in the stabilized projection images, which in turn may be generated based on 3D locations of the structures of interest and a known (static) visualization view angle, displacement maps, or combinations thereof. The geometric information is derived from one or more of the 2D projections, a 3D volumetric reconstruction, and a known imaging geometry. The known imaging geometry may be specified by a view angle and other geometric parameters of the imaging system.

Furthermore, the geometric information such as the displacement maps may be used to perform stabilization of at least one image sequence. As used herein, the term "stabilized image sequence" is used to refer to a synthesized image sequence that is generated with respect to a pre-defined view angle from an acquired sequence of projection images where structures of interest appear static in the stabilized images. One or more stabilized image sequences that include a set of stabilized images representing a 3D structure as seen from one or more associated static view angles, may be visualized on a display, for example. The stabilized image sequences provide a convenient display to the user. By way of example, the visualization of the stabilized image sequences simultaneously provides multiple view angles (perspectives) of the same device(s) and/or anatomical structures in real-time, thereby facilitating study and/or interpretation of the images by the user. In certain embodiments, images (which may include stabilized images) corresponding to anatomical context and/or interventional devices may be superimposed on the stabilized image sequences to provide a visualization of a spatial relationship between anatomy and the device(s). In one example, a temporal series of image sequences may be presented to the user. Also, in some embodiments, the anatomical context may include the vasculature.

In one embodiment, a stabilized image sequence corresponding to at least one visualization view angle may be displayed. Moreover, in some embodiments, the displayed stabilized image sequence may be generated by processing a first image sequence ("primary image sequence") using geometric information derived from a second image sequence ("auxiliary image sequence"). In certain embodiments, the auxiliary image sequence may be different from the primary image sequence. However, in certain other embodiments, the auxiliary image sequence may be the same as the primary (or first) image sequence or may be a subset thereof. Also, use of visualization view angles and perspectives for the creation of the stabilized image sequences that are not constrained to lie on the acquisition trajectory and hence do not have corresponding acquired projection data is also contemplated. In this manner, images of the imaged device(s) and/or anatomy may be generated that correspond to view angles or perspectives at which no projection data was actually acquired.

Also, in one embodiment, at least one stabilized image sequence is presented to the user in real-time (or near-real-time), thereby facilitating guidance of catheters and/or other devices within the imaged volume, for example. In accordance with further aspects of the present specification, the acquisition trajectory (for example, the projection view angles), the visualization view angles, corresponding update rates, and the like may be adaptively adjusted based on a region of interest (ROI) or the structures of interest contained therein, thereby facilitating real-time assessment. By way of example, gantry trajectory and/or the view angles for stabilized views may be adapted based on the local geometry of the vascular structure. As will be appreciated, depending on the position of a catheter tip within the vasculature, the local structure of the vasculature varies. In accordance with aspects of the present specification, the imaging and processing parameters may be adapted based on the local structure.

Also, the tomographic angle may be adapted for different acquisition conditions. By way of example, for acquisitions where a contrast agent is injected into the vasculature, a larger tomographic angle may be chosen. In this example, the gantry may traverse a bigger ellipse. However, for acquisitions where a catheter or other interventional devices are employed, a smaller tomographic angle may be selected. In this example, the gantry may traverse a smaller ellipse. It may be noted that each acquisition may include an entire orbit, a subset of an orbit, or more than one orbit (for example, multiple orbits). By way of example, image data corresponding to a continuous motion that includes a repeated traversal of an elliptical trajectory may be acquired. Although not every embodiment of the present specification encompasses a reconstruction of a volume image from the acquired sequence of projection images, the image acquisition is referred to as a tomosynthesis acquisition. Stabilized images for one or more visualization view angles may be presented to the user, thereby aiding the clinician in gaining an improved understanding of the 3D structure of the imaged anatomy and/or device(s). To further facilitate image interpretation, images of anatomy (which may also be stabilized image sequences or other image data) and stabilized image sequences of device(s) may be displayed superimposed (or in other well-defined spatial relationships) in order to provide appropriate anatomical context to the clinician.

Referring now to FIG. 1, a diagrammatical representation of a single-plane tomosynthesis imaging system 100 is presented. In a presently contemplated configuration, the system 100 includes an imaging unit 101 and a multi-perspective imaging platform 144.

The imaging unit 101 is configured to acquire X-ray attenuation data, where the X-ray attenuation data may be used for processing and/or reconstruction. The acquired image data may be representative of data corresponding to a target region in a subject such as a patient 108. In the embodiment illustrated in FIG. 1, the imaging unit 101 includes a source of X-ray radiation 102 and a detector 104. The X-ray source 102 may be an X-ray tube, a distributed X-ray source (such as a solid-state or thermionic X-ray source) or any other source of X-ray radiation suitable for the acquisition of medical or other images. X-rays 106 generated by the source 102 traverse a region in which the patient 108 is positioned during an imaging or diagnostic procedure. In one example, the X-rays 106 may be collimated to form a cone-shaped beam. This beam may pass through the imaged volume. A portion 110 of the X-ray radiation 106 passes through or around the patient 108 (or another subject of interest) and impacts a detector array, represented generally as the detector 104. Detector elements of the detector 104 produce electrical signals that represent the intensity of the portion of the incident X-rays 110. These signals are acquired and processed to represent images of the features within the patient 108. These images may generally be referred to as "projection images" or "projection views."

In certain implementations, the tomosynthesis acquisition operates such that the X-ray detector 104 and the source 102 (for example, an X-ray tube) orbit one or more times above and below the patient 108, respectively. For example, the source 102 and the detector 104 may each orbit within separate respective planes or other constrained 2D or 3D trajectories, one above and one below the patient 108. In one such implementation, the orbit may have a half tomographic angle in a range from about 15° to about 30° and an orbit period in a range from about 1.5 to about 3 seconds. As will be appreciated, CBCT imaging calls for a so-called spin acquisition, where the gantry performs a rotation of about 210 degrees about the imaged ROI. This rotation includes in particular the tube moving to a position above the table plane both at the start and at the end of the gantry rotation. Therefore, the tomosynthesis acquisition gantry motion has a significantly reduced footprint relative to other imaging modalities such as CBCT imaging and computed tomography (CT) imaging. Consequently, a tomosynthesis acquisition may also be performed even in circumstances that inhibit use of other imaging approaches. Some examples of the inhibiting circumstances include collisions with procedure room apparatus, the patient, and/or staff.

A continuous orbit and continuous projection data acquisition, when employed, provides timing flexibility for the procedure and imaging operation, such as manual injection, physiologic gating, selection of the bolus delay to be reconstructed, and the like. However, the present system and method may be employed when as little as a single orbit, a fraction thereof, or a subset of projection images from a single orbit of projection image data is acquired. In the present example, the source 102 and detector 104 may be a part of an imager subsystem 112. The imager subsystem 112 may be representative of an acquisition unit. Also, the source 102 and the detector 104, at rest, may be positioned generally along a direction, which may correspond to an anterior/posterior (AP) direction of the patient 108, in certain embodiments. For example, the imager subsystem 112 may be configured to acquire X-ray images or X-ray projection data over a limited angular range with respect to one side or facing (for example, the AP direction) of the patient 108.

The single-plane imaging system 100 of FIG. 1 is depicted as including a single source and single detector that are mounted on a movable gantry on opposite sides relative to the imaged ROI. However, in certain embodiments the imaging system may be a bi-plane imaging system that includes an additional source of X-ray radiation and an additional detector configured to acquire projection images at a different direction, location, and/or timing than the source 102 and detector 104. It may be noted that in such a bi-plane system, the first imaging plane may generally be adapted to acquire images where the projection directions are generally aligned with the posterior-anterior (PA) direction of the patient, while the second imaging plane may be adapted to acquire images where the projection directions are generally aligned with a lateral projection direction relative to the patient.

Furthermore, the imager subsystem 112 may be moved relative to the patient 108 or imaged object along one or more axes during an imaging procedure. Projection data may be acquired during the movement of the imager subsystem 112. For example, the imager subsystem 112 may move about a first axis of rotation 114, a second axis of rotation 116, or a third axis of rotation 118, or any combination thereof. In one embodiment, the translation and rotation of the imager subsystem 112 may be determined or coordinated in accordance with a specified protocol.

The movement of the imager subsystem 112 may be initiated and/or controlled by one or more linear positioning subsystems 120 and rotational subsystems 121. The linear positioning subsystems 120 and/or the rotational subsystems 121 may include support structures, motors, gears, bearings, and the like, that enable the rotational and/or translational movement of the imager subsystem 112 relative to the imaged object and/or patient. In one embodiment, the linear positioning subsystems 120 and/or the rotational subsystems 121 may include a structural apparatus such as a C-arm apparatus having rotational movement about at least two axes and configured to support the source and detector 102, 104.

A system controller 122 may govern the linear and/or rotational subsystems 120, 121 that initiate and/or control the movement of the imager subsystem 112. In practice, the system controller 122 may incorporate one or more processing devices that include or communicate with tangible, non-transitory, machine readable media collectively storing instructions executable by the one or more processors to perform the operations described herein. The system controller 112 may also include features that control the timing of the activation of the source 102, for example, to control the acquisition of X-ray attenuation data obtained during a particular imaging sequence. Furthermore, the system controller 122 may also be configured to execute various signal processing and filtration functions, such as for initial adjustment of dynamic ranges, interleaving of digital projection data, and the like. Therefore, in general, the system controller 122 may be configured to command operation of the imaging unit 101 to execute examination protocols. It should be noted that, to facilitate discussion, reference is made hereinafter to the system controller 122 as being the unit that controls acquisitions, movements, and the like, using the imager subsystem 112. However, embodiments where the system controller 122 acts in conjunction with other control devices such as other control circuitry local to the imager subsystem 112 or remote to the system 100 are also encompassed by the present specification.

In one embodiment, the system controller 122 may include signal processing circuitry and various other circuitry that enable the system controller 122 to control the operation of the imager subsystem 112 and the linear positioning subsystems 120 and/or the rotational subsystem 121. In the illustrated embodiment, the circuitry may include an X-ray controller 124 configured to operate the X-ray source 102 so as to time the operations of the source 102 and to interleave the acquisition of X-ray attenuation data as desired. Circuitry of the system controller 122 may also include one or more motor controllers 126. The motor controllers 126 may control the activation of various components that are responsible for moving the source 102 and the detector 104. By way of example, the motor controllers 126 may be configured to implement a particular trajectory for the imager subsystem 112.

In the example of FIG. 1, the system controller 122 is also illustrated as including one or more data acquisition subsystems 128. Generally, the detector 104 may be coupled to the system controller 122, and more particularly to the data acquisition subsystems 128. The data acquisition subsystems 128 may be configured to receive data collected by read-out electronics of the detector 104 and may be configured to process the data. In certain embodiments, the data acquisition subsystems 128 may be configured to process the data by converting analog to digital signals or by filtering and/or transforming the data.

The system controller 122 and the various circuitry associated components 124, 126, 128, as well as processing and memory components 130, 132, may be accessed or otherwise controlled by an operator via an operator workstation 134. The operator workstation 134 may include any application-specific or general-purpose computer that may include one or more programs (for example one or more imaging programs) capable of enabling operator input to perform the techniques described hereinafter. The operator workstation 134 may include various input devices such as a mouse, a keyboard, a trackball, or other similar features that enables the operator to interact with the system 100. The operator workstation 134 may enable the operator to control various imaging parameters, for example, by adjusting certain instructions stored on the memory devices 132.

The operator workstation 134 may be communicatively coupled to a printer 136 for printing images, patient data, and the like. Moreover, the operator workstation 134 may also be in communication with a display 138 that enables the operator to view various parameters in real-time, to view images produced by the acquired data, and the like. The operator workstation 134 may also, in certain embodiments, be communicatively coupled to a picture archiving and communication system (PACS) 140. Such a system may enable the storage of patient data, patient images, image acquisition parameters, and the like. This stored information may be shared throughout the imaging facility and may also be shared with other facilities, for example, a remote client 142. The remote client 142 may include hospitals, doctors' offices, or any other similar client.

Also, in the presently contemplated configuration illustrated in FIG. 1, the multi-perspective imaging platform 144 is shown as a standalone module that is physically separate from the imaging unit 101. In particular, the multi-perspective imaging platform 144 is external to and operatively coupled to the imaging unit 101. However, in certain other embodiments, the multi-perspective imaging platform 144 may be included as a component of the imaging unit 101.

The multi-perspective imaging platform 144 may be configured to facilitate a multi-perspective display (for example, display of images that correspond to one or more static view angles) of appropriately processed (warped) projection images acquired by a single plane interventional X-ray system. In particular, the multi-perspective imaging platform 144 may be configured to initiate acquisition of one or more image sequences corresponding to one or more tomographic angle sequences. It may be noted that images in the one or more image sequences may include one or more structures of interest such as opacified vasculature (that is, vasculature with injected contrast medium), catheters, needles, other devices, bones, and the like. It may be noted that due to the motion of the X-ray source (and/or the detector) relative to the imaged structures, the location and/or orientation of the structures of interest within the images change as the acquisition progresses, thereby making image interpretation difficult. According to aspects of the present specification, the images may be warped so as to represent one or more stabilized image sequences, where the structures of interest appear static within the image, as seen from a static view angle (generally one view angle for each stabilized image sequence), thereby facilitating enhanced image interpretation. By way of example, the enhanced image interpretation may be used for device guidance and the like.

Further, the multi-perspective imaging platform 144 may be configured to derive geometric information about structures of interest in the images from at least one image sequence. The image sequence that is used to derive the geometric information may be generally referred to as the "auxiliary image sequence." Also, the projection angles associated with the auxiliary image sequence may generally be referred to as "auxiliary tomographic angle sequence". The multi-perspective imaging platform 144 may be configured to generate one or more displacement maps based on the geometric information, a primary tomographic angle sequence, and other inputs such as visualization information, or combinations thereof.

Moreover, the multi-perspective imaging platform 144 may also be configured to transform/warp images in one or more image sequences based on corresponding displacement maps to create one or more warped image sequences. In some embodiments, the image warping using the displacement maps may be applied to the auxiliary image sequence. However, in certain other embodiments, the displacement maps may be used to warp a different image sequence. The image sequence being warped may generally be referred to as the "primary image sequence," and the associated projection angles may be referred to as the "primary tomographic angle sequence." In some embodiments, multiple image sequences may be warped, where the multiple image sequences may include the auxiliary image sequence and one or more other image sequences. The warped image sequences may be representative of "stabilized image sequences." As previously noted, the term "stabilized image sequence" is used to refer to an image sequence in which at least a subset of images is warped such that structures of interest appear as if viewed from a static pre-defined visualization view angle. Also, the multi-perspective imaging platform 144 may be configured to visualize the one or more stabilized image sequences on a display such as the display 138. It may be noted that the selected view angles as well as the acquisition angles may be adapted to best visualize the imaged structures of interest. In one embodiment, the acquisition and/or visualization view angles may be adapted in real time as the intervention (for example, navigation of a catheter or other device) progresses. In another embodiment, the acquisition and/or view angles may be selected or adjusted by the user. The working of the multi-perspective imaging platform 144 will be described in greater detail with reference to FIGS. 3-7.

It may be noted that the tangible, non-transitory, machine-readable media and the processors that are configured to perform the instructions stored on this media that are present in the system 100 may be shared between the various components of the system controller 122, the multi-perspective imaging platform 144 and/or other components of the system 100. For instance, as illustrated, the X-ray controller 124, the motor controller 126, and the data acquisition subsystems 128 may share one or more processing components 130 and/or the multi-perspective imaging platform 144, where each component may be specifically configured to cooperate with one or more memory devices 132 storing instructions that when executed by the processing components 130 and/or the multi-perspective imaging platform 144, facilitate the multi-perspective imaging described hereinafter. Further, the processing components 130, the multi-perspective imaging platform 144, and the memory components 132 may be configured to coordinate with one another in order to perform various processes. Also, the system controller 122, the processing components 130, the multi-perspective imaging platform 144, and the memory components 132 may generally be referred to as a processing unit.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the present specification. Thus, those skilled in the art will appreciate that the present imaging system 100 is provided by way of example, and the present specifications are in no way limited by the specific system configuration.

Figure 2:
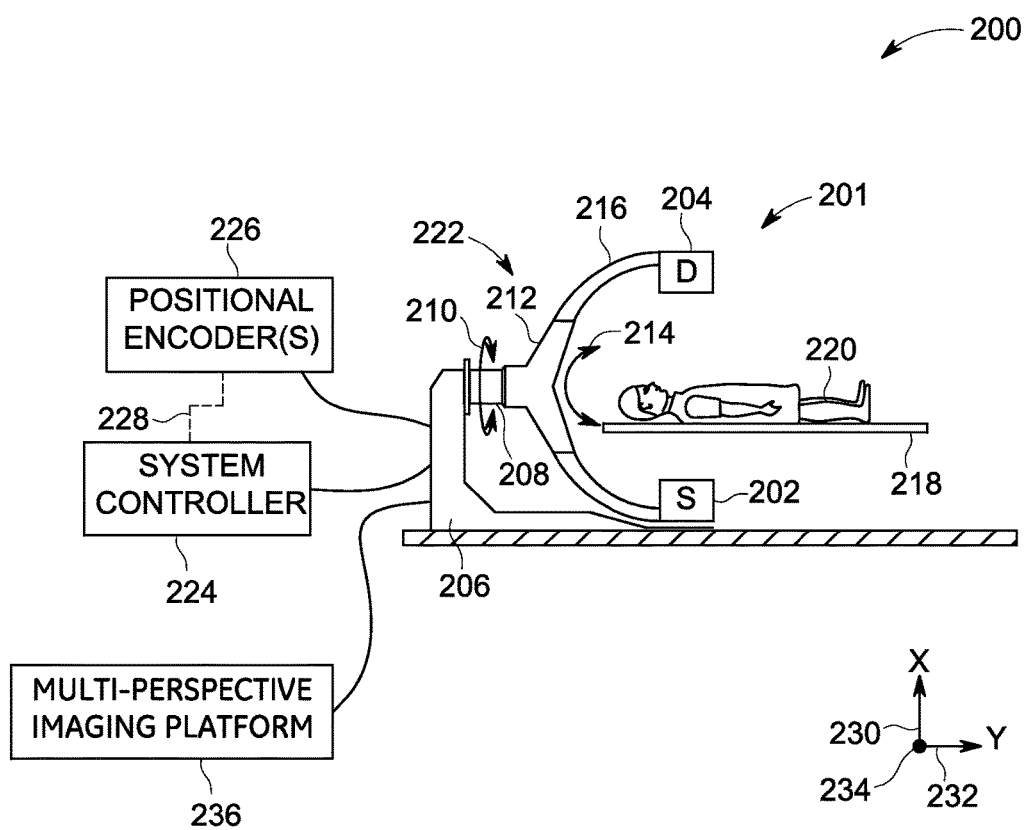
FIG. 2 is a side view of a single-plane imaging system configured to acquire projection data along a plane via rotation about two axes, in accordance with aspects of the present specification.

FIG. 2 is a diagrammatical representation 200 of one embodiment of the system 100 of FIG. 1. In one example, the system 200 is a single-plane C-arm imaging system configured for tomosynthesis imaging. Furthermore, in a presently contemplated configuration, the imaging system 200 includes a single-plane imaging unit 201 and a multi-perspective imaging platform 236.

In the embodiment of FIG. 2, the imaging unit 201 includes a base 206 and a rotatable extension 208 extending from the base 206. In the illustrated embodiment, the base 206 is a floor-mounted base such that the imaging unit 201 may be secured to a floor of an imaging area in which it is positioned. In other embodiments, however, the base 206 may be secured to other surfaces (for example, a wall or ceiling) and/or may be mobile or movable.

The rotatable extension 208 is depicted as extending generally along a second axis of rotation 232. Furthermore, the rotatable extension 208 may be configured to enable a source 202 and a detector 204 to move about the second axis of rotation 232. For example, the rotatable extension 208 may be configured to enable the source 202 and the detector 204 to move about the second axis of rotation 232 in a manner that maintains the positions of the source 202 and detector 204 relative to one another throughout the movement of the rotatable extension 208. The rotation enabled by the rotatable extension 208 is shown as double-headed arrow 210. The rotatable extension 208 is coupled to a moving structure 212, which is configured to enable the source 202 and the detector 204 to move about a third axis of rotation 234. This rotation about the third axis of rotation 234 is depicted as double-headed arrow 214. The source 202 corresponds to the source 102 of FIG. 1, while the detector 204 corresponds to the detector 104 of FIG. 1. Moreover, a patient 220 corresponds to the patient 108 of FIG. 1.

The moving structure 212 may be a geared or track structure that is movably coupled to a support structure 216 that physically supports the source 202 and the detector 204, and may be in the form of a C-arm, or any other shape that positions the source 202 and the detector 204 on either side of the patient 220. As depicted in FIG. 2, the support structure 216 includes an arcuate structure that extends from a first side of a patient table 218, around the patient table 218, and to a second side of the patient table 218. In this way, the source 202 and the detector 204 generally remain positioned at opposite ends and/or on opposite sides of the patient 220 positioned on the patient table 218. Together, the base 206, the rotatable extension 208, the moving structure 212, and the support structure 216 may be generally referred to as the structure 222 of the imaging unit 201.

The imaging unit 201 may include various motors, actuators, or other features responsible for movement of the various structures of the imaging unit 201. These components may be communicatively coupled to one or more positional encoders 226. The one or more positional encoders 226 may be configured to encode the respective positions of any of the one or more components of the imaging unit 201 in a manner that facilitates processing by a system controller 224. The system controller 224 corresponds to the system controller 122 of FIG. 1. In such an implementation, the positional encoders 226 may be configured to provide feedback 228 (for example via wired or wireless signals) to the system controller 224.

The system controller 224 may be configured to use this feedback 228 to control the imaging system 200. By way of example, the system controller 224 may be configured to simultaneously move the source 202 and the detector 204 together about a first axis of rotation 230, the second axis of rotation 232, or the third axis of rotation 234, or any combination thereof, and obtain X-ray attenuation data such as projection images or projection views corresponding to the set (or a subset) of traversed view angles. In one embodiment, the system controller 224 may be configured to receive positional information from the positional encoders 226 relating to an imager subsystem such as the imager subsystem 112 of FIG. 1 and calculate a trajectory (or update a modeled trajectory) for the source 202 and/or the detector 204 using this positional feedback information 228.

The imaging system 200 may be configured to perform an acquisition of data using an acquisition trajectory such as a circular path, an ellipsoidal path, or similar paths traced by the source 202 below the patient 220 and a corresponding circular, ellipsoidal, or similar paths traced by the detector 204 above the patient 220. The system 200 may also be configured to acquire data for different orientations of the planes that may generally be used to describe the orientation of these trajectories, where the imaged ROI generally is positioned between the source and the detector planes. Furthermore, in one embodiment, the system controller 224 may be configured to synthesize one or more volumetric images using the data obtained by the imaging system 200 and the imaging unit 201 in particular. Tomosynthesis reconstruction algorithms (such as filtered back projection or other reconstruction algorithms) may be used to reconstruct a 3D volumetric image of the imaged region of interest.

Moreover, imaging system 200 may include the multi-perspective imaging platform 236. The multi-perspective imaging platform 236 corresponds to the multi-perspective imaging platform 144 of FIG. 1. In one embodiment, the multi-perspective imaging platform 144, 236 (see FIGS. 1-2) may be configured to perform the methods of FIGS. 3-8.

Additionally, the various components may be dedicated hardware elements such as circuit boards with digital signal processors or may be software running on a general-purpose computer or processor such as a commercial, off-the-shelf personal computer (PC). The various components may be combined or separated according to various embodiments of the present specification. Thus, those skilled in the art will appreciate that the present imaging system 200 is provided by way of example, and the present specifications are in no way limited by the specific system configuration.

Figure 3:
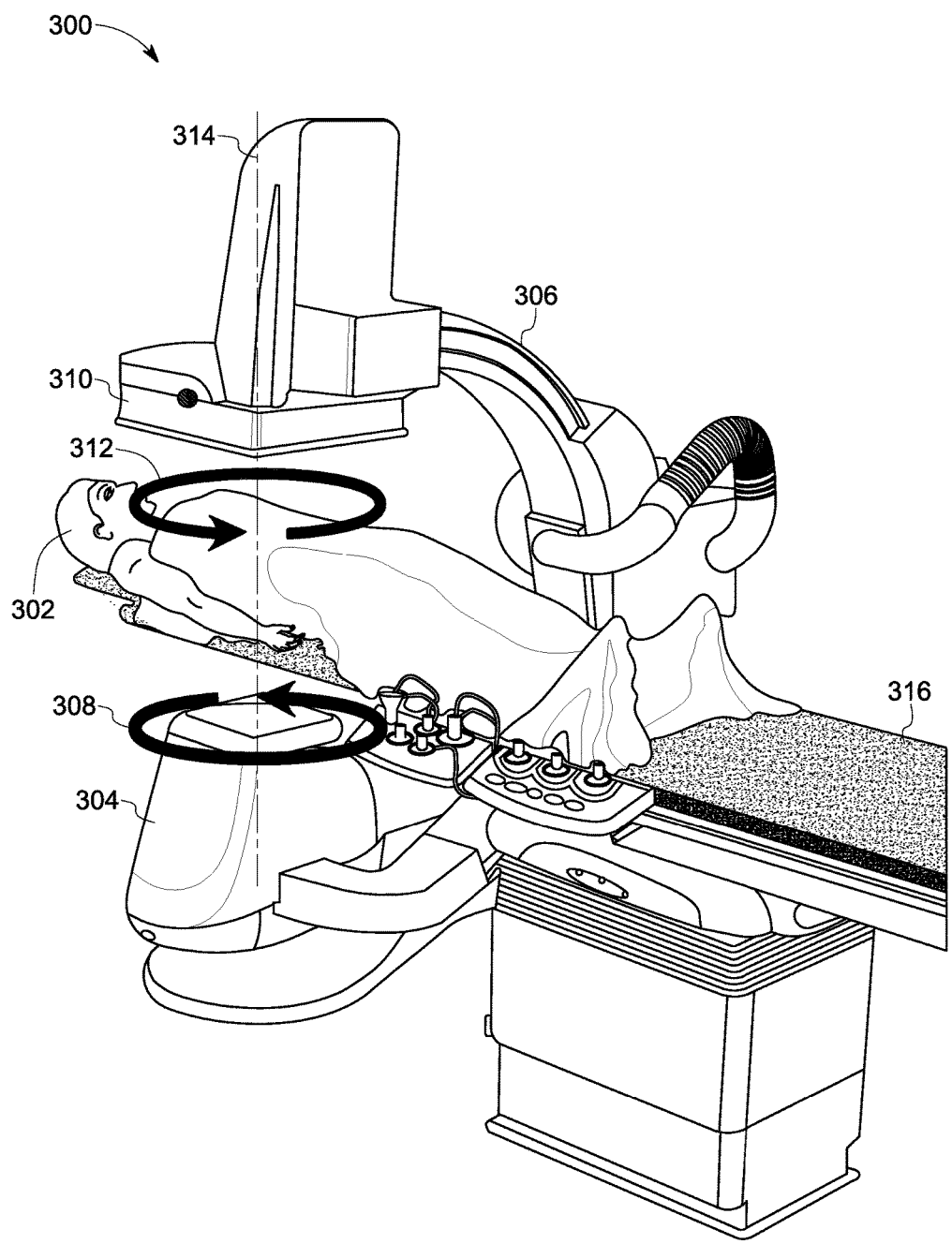
FIG. 3 is a diagrammatical representation of a single-plane C-arm tomosynthesis imaging system configured to perform multi-perspective imaging, in accordance with aspects of the present specification.

FIG. 3 is a diagrammatical representation of one example of an imaging system 300 such as the imaging system 200 of FIG. 2. In particular, a perspective view 300 of the single-plane C-arm tomosynthesis imaging system 200 (see FIG. 2) is depicted in FIG. 3. The imaging system 300 may be configured to perform multi-perspective imaging of one or more structures of interest in a patient such as a patient 302. In particular, FIG. 3 depicts an exemplary motion of the imaging system 300 to facilitate acquisition of one or more image sequences.

The motion of the imaging system 300, as depicted in FIG. 3 may be representative of an orbit of the imaging system 300, which may be traversed one or more times as part of the gantry trajectory during acquisition of one or more image sequences. In this example, the imaging system 300 may be configured to obtain projection data from a plurality of projection directions (also referred to as projection angles or view angles). These projection directions may be limited by an angular range of motion of the imaging system 300. The angular range of motion may also be restricted by presence of proximate structures and/or personnel. In one embodiment, the angular range of the trajectory may also be limited due to temporal constraints. In one example, the angular range of an elliptical orbit that is part of the trajectory may be defined by the requirement that the orbit may have to be traversed in a determined amount of time, for example, in about 3 seconds or less. In one embodiment, the X-ray source is constrained to move on a first side of the imaged volume and the X-ray detector is constrained to move on a second side of the imaged volume opposite of the first side.

Moreover, as used herein, the term "orbit" or "trajectory" of an imaging system is used to refer to a path traced by an X-ray source during image acquisition. A trajectory of the imaging system typically entails moving the source within this limited angular range with respect to an imaged subject such as the patient. Furthermore, the configuration depicted in FIG. 3 illustrates an example where the tube moves generally in a plane below the patient, and the detector moves generally in a plane above the patient. More generally, while FIG. 3 illustrates trajectories of the source (or detector) located generally in planes below (or above) the patient (with the projection direction generally in the anterior-posterior (AP) direction), use of other orientations of these planes is also contemplated. Some examples of these other orientations include a direction generally oriented in a lateral direction or an oblique direction, and the like.

Consequently, in order to facilitate acquisition of tomographic data, an X-ray source such as the source 304 may be configured to move in a plane on one side of a patient 302. For example, the X-ray source 304 may be moved in a circular or elliptical/oval motion in front of the patient 302 without rotating around the patient 302, and X-ray projection data corresponding to a limited angular range with respect to the patient 302 may be acquired. Reference numeral 308 is generally representative of a direction of rotation of the source 304, while a direction of rotation of the detector 310 is generally represented by reference numeral 312.

Typically, a range of motion of the tomographic trajectory is in a range from about +30 degrees to about −30 degrees of a central axis (for example, the AP direction), and may include a periodic motion of a C-arm 306. In FIG. 3, an elliptical trajectory with a central axis 314 in the AP direction is shown. In one such imaging mode, the detector 310 and the source 304 may be configured to orbit one or more times within respective planes above and below a patient table 316. In one embodiment, the orbit generally corresponds to a half tomosynthesis angle in a range between about 15 degrees and about 30 degrees and an orbit may be traversed in a range of about 1.5 seconds to about 3 seconds. The term half-angle generally refers to the angle between a specific view direction and the direction of the central axis 314. In some embodiments, such trajectories may be periodic in that the path traced by the X-ray source 304 may be repeated throughout the examination. By way of example, the C-arm 306 may be configured to traverse the same elliptical orbit multiple times. In another embodiment, the orbit may be changed at different times to create smaller or larger elliptical orbits. This change in the size/diameter of the orbits may result in corresponding changes in respective tomographic angles and/or times per orbit.

Moreover, in accordance with aspects of the present specification, the central axis 314 of the tomographic acquisition may be changed. More particular particularly, the central axis 314 of the tomographic acquisition may be changed as a function of the local structure being imaged. In addition, in some embodiments, although the C-arm 306 may be moved in a continuous manner, image data may be acquired intermittently. Also, other parameters such as an image acquisition rate, a frame rate, and the like may also be adapted based on current imaging conditions.

In accordance with aspects of the present specification, image data may be acquired during a single orbit. However, in certain embodiments, image data corresponding to a determined portion or a subset of a single orbit may be acquired, or image data may be acquired during multiple orbits. The central view axis for the image acquisition may be adapted to the geometry of the imaged structure. Furthermore, a tomographic angle may also be adjusted based on the currently selected "mode." For instance, imaging of the interventional device alone may use smaller tomographic angle(s), while imaging with injected contrast may use a larger tomographic angle in order to better capture the entire 3D vascular structure and geometry. Additionally, in situations that call for resolution of soft tissues, for example at or near the tip of a biopsy needle or ablation device, use of a larger tomographic angle may be beneficial. Continuous motion of the C-arm 306 permits different acquisition modes including imaging of the interventional device only, contrast injection to understand local vasculature, subtracted images (for example, digital subtraction angiography (DSA)) to remove static background from images, and the like. In one example, the static background may include soft tissue and bones. The image data so acquired provides an image sequence of a three-dimensional (3D) anatomical region in the patient 302, which may then be processed according to aspects of the present specification to provide one or more stabilized image sequences to the user. In another embodiment, continuous gantry motion may be used for continuous visualization during an ongoing procedure to provide continuous visualization/support of an ongoing procedure.

Figure 4:
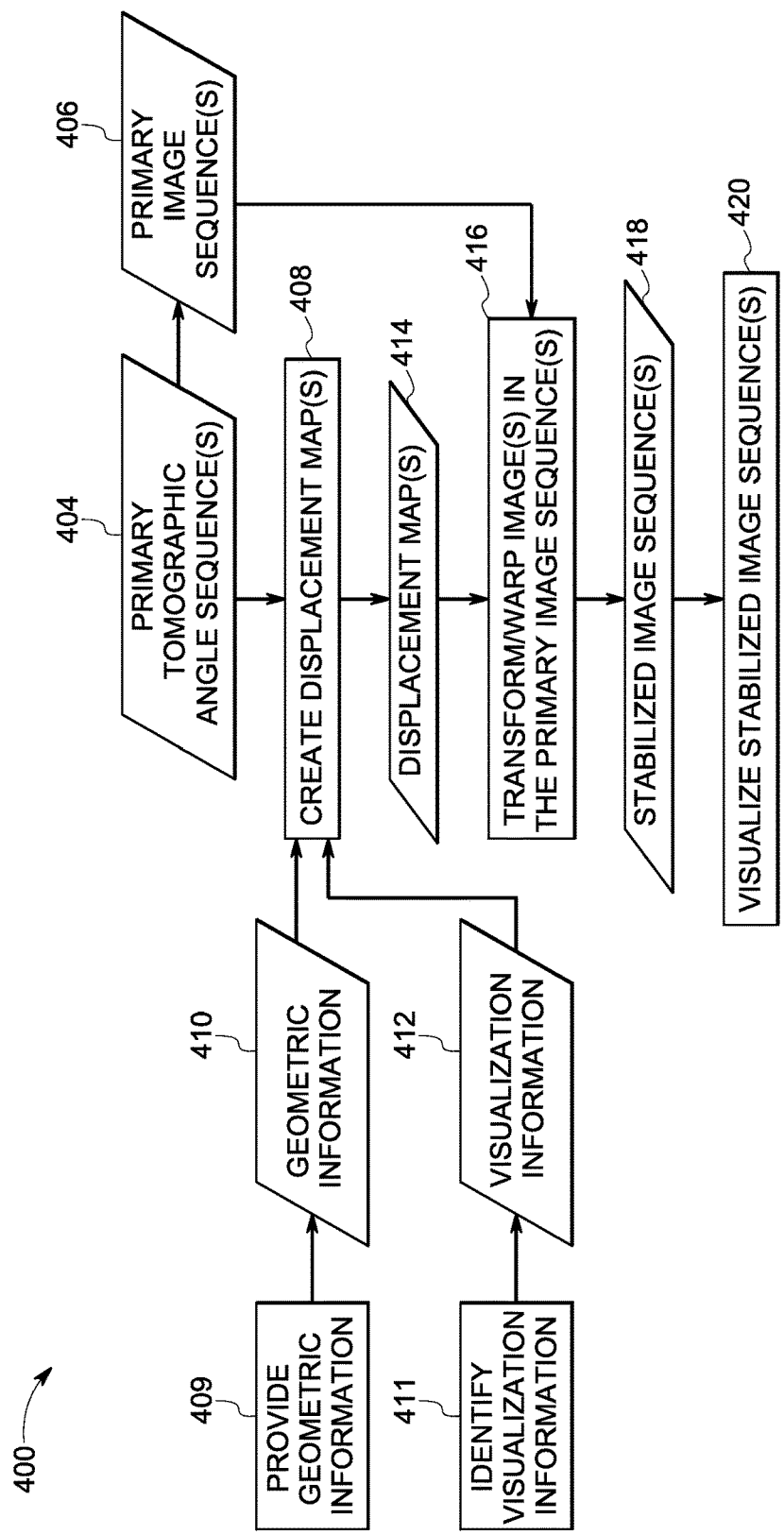
FIG. 4 is a flow chart depicting an exemplary method for multi-perspective interventional imaging, in accordance with aspects of the present specification.

Turning now to FIG. 4, a flow chart 400 depicting a method for multi-perspective interventional imaging, in accordance with aspects of the present specification, is presented. In one embodiment, one or more tomographic angle sequences may be selected. Subsequently, one or more image sequences may be acquired corresponding to the one or more tomographic angle sequences. Reference numeral 404 is generally representative of the one or more tomographic angle sequences. In one example, the one or more tomographic angle sequences 404 may be referred to as "primary tomographic angle sequence(s)." Also, the corresponding one or more image sequences may be referred to as "primary image sequence(s)", and are generally represented by reference numeral 406.

In certain embodiments, at least one of the one or more tomographic angle sequences 404 may be selected such that a source (for example, the source 304) of an imaging system (for example, the imaging system 300 of FIG. 3) is constrained to move about a first side of a target region being imaged in a patient (for example, the patient 302) and a detector (for example, the detector 310) of the imaging system is configured to move about a second side of the target region, where the second side is opposite the first side.

Also, the one or more image sequences 406 may be representative of a target region in a subject such as the patient 220 (see FIG. 2). Further, each of the one or more image sequences 406 may in turn include one or more images.

Moreover, as indicated by step 409, geometric information 410 corresponding to one or more structures of interest in at least one of the one or more image sequences 406 may be provided. In one embodiment, the geometric information 410 may include 3D location information regarding the one or more structures of interest in the imaged volume. Some examples of the structures of interest include, but are not limited to, opacified vasculature, catheters, needles, other devices, bones, and the like. The geometric information may also include displacement information associated with a 2D-2D registration of the images in the auxiliary image sequence.

In addition, at step 411, visualization information 412 may be identified. The visualization information 412 may include one or more visualization view angles. By way of example, the user such as a clinician may provide the visualization information 412 via the operator workstation 134 of FIG. 1. In accordance with aspects of the present specification, the system 100 (see FIG. 1) may be configured to allow the user to define and/or update the visualization view angles. Moreover, the system 100 may also be configured to allow the user to define and/or update scanning parameters such as gantry trajectory, the central view axis and the tomographic angle, frame rate, and the like.

In accordance with exemplary aspects of the present specification, at step 408, one or more displacement maps may be generated. More particularly, in one embodiment, the displacement maps may be created based on the geometric information 410, the visualization information 412, at least a subset of at least one of the one or more primary tomographic angle sequences 404, or combinations thereof. Reference numeral 414 is generally representative of the displacement map(s). The derivation of the geometric information 410 and the creation of the displacement maps 414 will be discussed in greater detail hereinafter with reference to FIGS. 6 and 7.

Subsequently, at step 416, at least a subset of images in the one or more primary image sequences 406 may be warped/transformed based on corresponding displacement maps 414 to create one or more transformed/stabilized image sequences. In particular, the displacement maps 414 may be used to generate a warped or "stabilized" image sequence 418 corresponding to a given visualization view angle. As previously noted, the term stabilized image sequence is used to refer to an image sequence where structures of interest in the stabilized images appear static with respect to a pre-defined visualization view angle. Accordingly, at step 416, one or more images in the one or more primary image sequences 406 may be warped to generate at least one warped or stabilized image sequence 418. More specifically, the displacement map 414 may be used to warp the one or more images in the one or more primary image sequences 406 such that the structures of interest in the resulting warped images appear as being viewed from a static view angle to generate the stabilized image sequences 418. In some embodiments, all the projection images corresponding to the one or more primary image sequences 406 or a subset thereof may be warped to one or more user-specified visualization view angles via use of corresponding displacement maps 414 to create corresponding stabilized image sequences 418.

Furthermore, at step 420, at least the stabilized image sequence(s) 418 may be visualized on a display, thereby providing a stabilized presentation of the imaged structures in the target region. As used herein, the term "stabilized presentation" is used to refer to a visualization/display of the stabilized image sequence 418. It may be noted that the terms stabilized presentation, stabilized display, and display of the stabilized image sequence may be used interchangeably. It may be noted that in the present example of FIG. 4 use of two or more visualization view angles is envisioned to provide a multi-plane view or multi-perspective view.

Furthermore, in accordance with aspects of the present specification, displacement maps corresponding to more than one visualization view angle may be created. These displacement maps may then be used to create and display stabilized image sequences for each considered visualization view angle. In one example, in order to provide a multi-perspective presentation to the user, one of the visualization view angles may be selected such that that visualization view angle 412 is in a range from about 60 degrees to about 90 degrees from at least one other visualization view angle.

The stabilized image sequences for multiple visualization view angles provide the user with a view of the structure of interest from multiple visualization view angles, based on a projection image sequence acquired with a single imaging system. Providing these multiple (two or more) view angles affords the user a benefit that is similar to benefits provided by a standard bi-plane system. By way of example, 3D information about the imaged structures may be conveyed by displaying multiple 2D image sequences (i.e., stabilized image sequences) that correspond to different view angles.

In one embodiment, images in one image sequence (the "primary image sequence") may be warped based on corresponding displacement maps which were derived based on another image sequence (the "auxiliary image sequence") that is different from the primary image sequence; thereby creating a stabilized image sequence (for example, a warped primary image sequence) for each visualization view angle. For example, the other image sequence (the auxiliary image sequence) may correspond to opacified vasculature and is used to derive displacement maps that may be used, for example, for creating stabilized images of the vasculature. Subsequently, an image sequence of a catheter (or other interventional devices) that is being navigated through the vasculature (without injected contrast medium) may be acquired and stabilized using the previously derived displacement maps. In one embodiment, images corresponding to the vasculature and images corresponding to a catheter/interventional device in the vasculature may be arranged in a spatial relationship to generate a simultaneous display of the images. For example, a side-by-side display or a superimposed display of the two stabilized image sequences may show the relative position of the catheter/interventional device within the vasculature. Providing a similar display for multiple visualization view angles gives the user a multi-perspective view of both the catheter/interventional device and the vasculature.

Processing the image sequence as described herein above aids in customizing the image sequence based on user-specified inputs for presentation to the user. By way of example, in certain embodiments, all the images in the one or more primary image sequences may be stabilized and presented to the user. In accordance with further aspects of the present specification, one or more subsets of stabilized projection images corresponding to the acquisition trajectory may be presented to the user. In other embodiments, a subset of projection images that is "closest" to a given visualization view angle may be stabilized with respect to that visualization view angle and displayed. Additionally, in certain embodiments, the visualization view angle of the displayed projection image(s) may be annotated on the display or otherwise presented. Furthermore, at least one of the displayed image sequences may be configured to show anatomical/device context. In one example, the displayed image sequence may include a standard X-ray view that is selected from the acquisition trajectory. In another example, the anatomical context may be provided by displaying a volumetric image (for example, as a volume rendering or cross-sectional data at the location of interest, and the like) where the volumetric image is reconstructed from a set of projection images by using a tomosynthesis reconstruction algorithm.

Presenting image sequences to the user that correspond to two or more visualization view angles aids the user in inferring 3D information from the displayed views, which may in turn facilitate enhanced navigation of interventional devices within complex 3D vasculature. In one embodiment, the image warping and display is performed in near-real-time, thereby enabling immediate visual feedback to the user, from multiple fixed perspectives, which supports, for example, real-time placement and navigation of devices by the user. Various steps of FIG. 4 will be described in greater detail with reference to FIGS. 5-7.

Further, in FIG. 4, the exemplary method is illustrated as a collection of blocks in a logical flow chart, which represents operations that may be implemented in hardware, software, or combinations thereof. The various operations are depicted in the blocks to illustrate the functions that are performed in the exemplary method. In the context of software, the blocks represent computer instructions that, when executed by one or more processing units, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein.

In the present specification, embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract data types.

Additionally, embodiments of the exemplary method may also be practised in a distributed computing environment where optimization functions are performed by remote processing devices that are linked through a wired and/or wireless communication network. In the distributed computing environment, the computer executable instructions may be located in both local and remote computer storage media, including memory storage devices.

The method 400 may be described in a general context of computer executable instructions. Generally, computer executable instructions may include routines, programs, objects, components, data structures, procedures, modules, functions, and the like that perform particular functions or implement particular abstract data types. In certain embodiments, the computer executable instructions may be located in computer storage media, such as the memory 132 (see FIG. 1), local to the imaging system 100 (see FIG. 1) and in operative association with a multi-perspective imaging platform 144 (see FIG. 1). In certain other embodiments, the computer executable instructions may be located in computer storage media, such as memory storage devices, that are removed from the imaging system. Moreover, the method for multi-perspective interventional imaging includes a sequence of operations that may be implemented in hardware, software, or combinations thereof.

Figure 5:
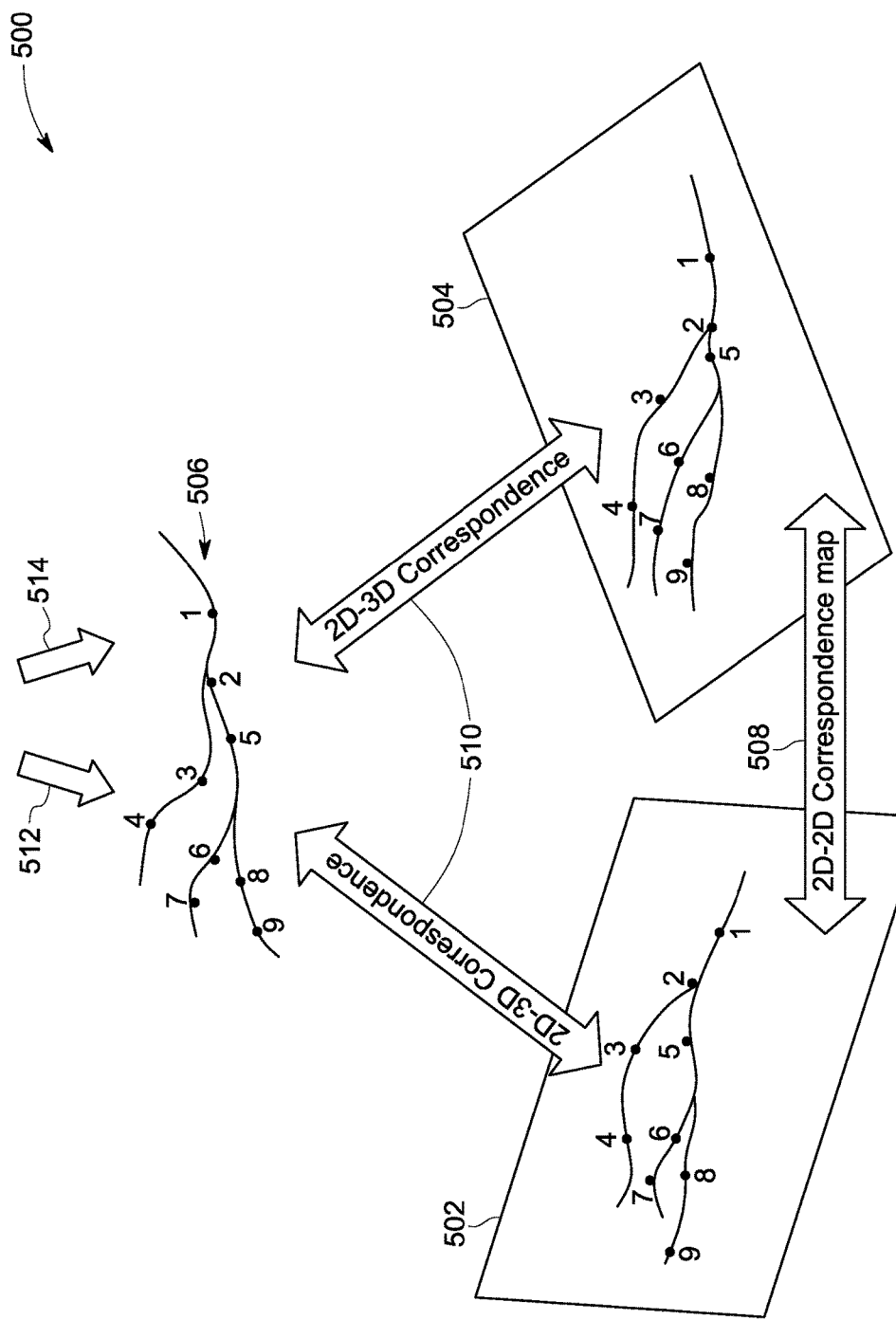
FIG. 5 is a diagrammatical illustration of underlying spatial and geometrical relationships that facilitate generation of a 2D-2D displacement map, in accordance with aspects of the present specification.

FIG. 5 is an illustration of underlying spatial and geometric relationships between a 3D object or structure contained in an imaged region of interest (ROI), the associated locations within each projection image, as well as the 3D locations in the imaged volume (or a reconstructed volumetric image of the imaged object). These relationships allow creation of the displacement maps. The creation of the displacement maps will be discussed in greater detail with reference to FIGS. 6 and 7.

In particular, FIG. 5 illustrates correspondences between locations of points of a given structure and respective locations in projection images associated with different view angles. The relationships between locations of points in the projection views in turn determine the displacement maps that facilitate warping of a projection image such that the structure in the warped image appears as it would appear if being viewed from a different view angle. In one example, one projection image (associated with one projection angle) may be warped such that the structure of interest in the warped image appears as if that structure is in a projection image associated with a different projection angle.

With continuing reference to FIG. 5, reference numeral 506 is generally representative of a 3D structure of interest. In the present example, the structure of interest 506 may include a vascular tree. Furthermore, reference numerals 502 and 504 are representative of two projection views/images of the structure of interest 506 or the region of interest that includes the structure of interest 506. The two projection images 502, 504 may be obtained by projecting the structure of interest 506 with respect to two different projection/view angles, as indicated by arrows 512, and 514, respectively. For ease of explanation, the projection image 502 is referred to as a first projection image, while the projection image 504 is referred to as a second projection image. It may be noted that in FIG. 5, for illustration purposes, sets of corresponding points in each domain are labelled using the same number. By way of example, a point labelled "1" in the 3D domain corresponding to a point location on the vascular tree 506 has a corresponding point labelled "1" in each of the two projection images 502, 504. Similarly, triplets of corresponding points, one in each of the two projection images 502, 504, and one in the 3D domain of the vascular tree 506 are labelled as "2," "3," "4," "5," "6," "7," "8," and "9", respectively.

In accordance with exemplary aspects of the present specification, 2D-2D correspondences may be employed to create displacement maps. These displacement maps may in turn be used to warp one image such that the structures visible in the warped image appear as being viewed from a different view angle. In certain embodiments, this 2D-2D correspondence may be derived directly. In one such embodiment, the 2D-2D correspondence may be derived by processing projection images/views that correspond to the two projection/view angles. However, in another embodiment, the 2D-2D correspondence may be derived by using knowledge of the locations of the corresponding points in the 3D domain, which may be obtained by computing a 3D reconstruction of the imaged volume.

After the 2D-2D correspondence between all the points (or a subset thereof) corresponding to the structure of interest 506 in the two projection images 502, 504 is determined, a mapping between the projection images 502, 504 may be established. The mapping may be referred to as a displacement map. This displacement map may generally be representative of the manner in which each point in one projection image needs to be displaced such that that point is translated to its corresponding location in a second image. By way of example, such a displacement map may include information regarding displacement/translation of point "1" in one projection image to the corresponding location "1" in another projection image. Additionally, the displacement map may also include information regarding similar mappings for all other pairs of corresponding points in the projection images. By combining this information for a number of corresponding point pairs, a displacement map for the whole image or at least for a region containing the structure of interest may be generated. In certain embodiments, the displacement map corresponding to at least the region that includes the structure of interest may be generated.

Use of such a displacement map aids in "warping" one projection image such that the resulting warped image depicts the structure of interest 506 as if the structure of interest is being viewed from a visualization view angle corresponding to the other projection image. In particular, the image 502 is warped such that the location of point "1" in the warped image 502 matches the location of point "1" in image 504. Similarly, the location of all (or a subset of) the other labelled points in the warped image 502 matches the location of corresponding points in image 504. Consequently, the structure in the warped image 502 may appear like the structure is being viewed from the view angle 514 that corresponds to the image 504. In the example of FIG. 5, reference numeral 508 is generally representative of a set of pair correspondences which defines a displacement map for transforming the first projection image 502 such that the structure of interest in the warped image is presented as if the structure of interest is viewed from the second projection angle 514.

As noted hereinabove, a single projection image 502 may be warped such that the imaged structure in the warped image appears as if viewed from projection angle 514 (associated with the projection image 504). In accordance with further aspects of the present specification, this process of warping the image may be extended to an image sequence which includes a plurality of images. More specifically, if a projection image sequence that includes the first projection image 502 is acquired where the associated projection angle 512 is varying over time, corresponding displacement maps may be derived from the corresponding 2D-2D correspondences. Subsequently, each image in the projection image sequence may be warped such that the structure of interest appears as if the structure of interest is being viewed from the static view angle 514. Such an image sequence associated with a varying projection angle may be acquired, for example, in a tomosynthesis image acquisition, where the gantry is moving along the tomosynthesis trajectory while X-ray images are being acquired. In such an embodiment, each view angle generally has its own correspondence and associated displacement map. It may be noted that in practice the projection angle 514 corresponds to a visualization view angle, and the acquired images are warped such that the resulting stabilized image sequence presents the imaged structures as if the imaged structures are being viewed from the visualization view angle 514. In one embodiment, such a stabilized image sequence is generated for more than one visualization view angle 514.

Moreover, as illustrated in FIG. 5, 2D-2D relationships (for example, relationships between projection images) may be used to derive 2D-2D correspondences and corresponding displacement maps directly. In accordance with some aspects of the present specification, such a 2D-2D correspondence may be established by directly using projection images 502, 504 that correspond to the two projection angles 512 and 514. In particular, the 2D-2D correspondence may be established by performing a 2D-2D non-rigid registration between pairs of projection images. In this example, the 2D-2D non-rigid registration may be performed, while circumventing the need for explicit use of a 3D model. It may be noted that in this example, since a non-rigid registration step may only be performed for acquired projection views, visualization view angles may only be selected from the set of view angles that are used to acquire data. Consequently, stabilized image sequences may only be created for such visualization view angles. The creation of the associated displacement maps based on the 2D-2D non-rigid registration of pairs of projection images will be described in greater detail with reference to FIG. 7.

In accordance with further aspects of the present specification, displacement maps between projection images/views may be established with the help of a 3D representation of the structure of interest. In one embodiment, a 3D representation (or a 3D model) of the structure of interest may be established by using a reconstruction of a volumetric image, followed by an extraction of structures of interest. The structures of interest may be extracted via use of a segmentation technique. Alternatively, the structures of interest may be extracted by identifying/segmenting the structures of interest in the 2D projection views, followed by a reconstruction of 3D positions of the structures of interest. In one example, a triangulation method may be used to reconstruct the 3D positions of the structures of interest from the respective locations within the 2D images.

By way of example, given a point in the 3D domain 506, the known projection geometries associated with the projection images 502, 504 may be used to determine locations of that point in any two projection images such as the first and second projection images 502, 504 corresponding to that structure of interest. The locations of these points in the two projection images 502, 504 establish a correspondence between corresponding sets of points in the two projection images 502, 504. This correspondence in turn may be used to determine an associated displacement map. By way of example, a location of a point labelled "1" in the 3D model 506 may be considered. Based on the known projection angles 512 and 514 or more generally, the known projection geometry associated with the projection angles 512 and 514, the locations of that point (point "1") in each of the respective projection images 502, 504 may be computed. This relationship, in combination with similar relationships for the other points located on the 3D model, defines a set of 2D-2D correspondences, which in turn may be used to derive the corresponding displacement map. Reference numeral 510 is generally representative of a 2D-3D correspondence. This 2D-3D correspondence 510 is representative of a correspondence between locations of points in 3D, and the respective locations in the projection images. Also, this correspondence 510 is defined by the respective projection geometries associated with the projection angles 512 and 514. The determination of the 2D-2D correspondence via use of the 3D locations, and the creation of the associated displacement maps will be described in greater detail with reference to FIG. 6.

It may be noted that the example presented hereinabove is described with reference to two projection views/images that are used to create the 3D model of the imaged structure of interest. However, use of more than two projection images to generate an accurate 3D geometric representation of the structures of interest is also envisaged.

According to one aspect of the present specification, in one embodiment the 2D-3D correspondences 510 that provide 2D-2D correspondences which are then used to create displacement maps are derived based on use of the 3D model. Use of the 3D model in this example consequently allows mapping of acquired projection images to view angles that lie outside of the current acquisition trajectory, since the corresponding points in these projection images may be calculated based on the 3D model and an assumed arbitrary projection geometry. In particular, use of the 3D model allows creation of stabilized image sequences corresponding to visualization view angles that are not used to acquire projection data. More specifically, stabilized image sequences for view angles that are more than 15 degrees from the closest projection angle on the gantry trajectory may be generated.

The term "known projection geometries" for a given view angle is used to refer to a known source position and a known detector position and orientation, which is assumed to be known. For example, the imaging geometry may be derived from a given view angle via use of a geometric model of the system, which is assumed to be known. Alternatively, the imaging geometry may, for example, be derived by a calibration method. In the calibration method, a specific calibration phantom is placed in the field of view and projection views are acquired for various view angles, followed by extraction of a specific imaging geometry for each view. Generally, for each view angle or projection angle, there is an associated imaging geometry, and the view angle is considered to be representative of that imaging geometry.

Figure 6:
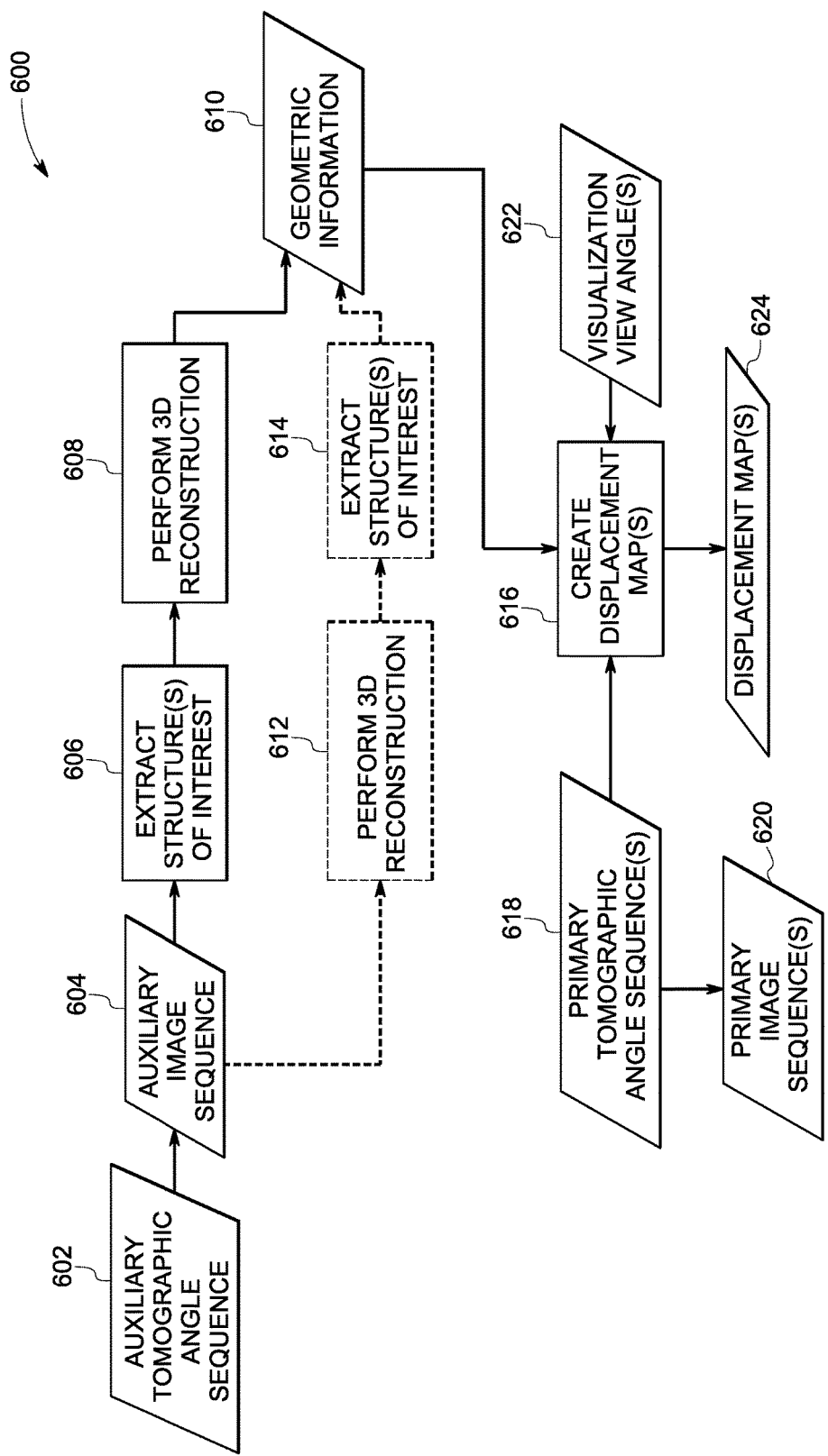
FIG. 6 is a flow chart depicting an exemplary method for generating a displacement map, in accordance with aspects of the present specification.
Figure 7:
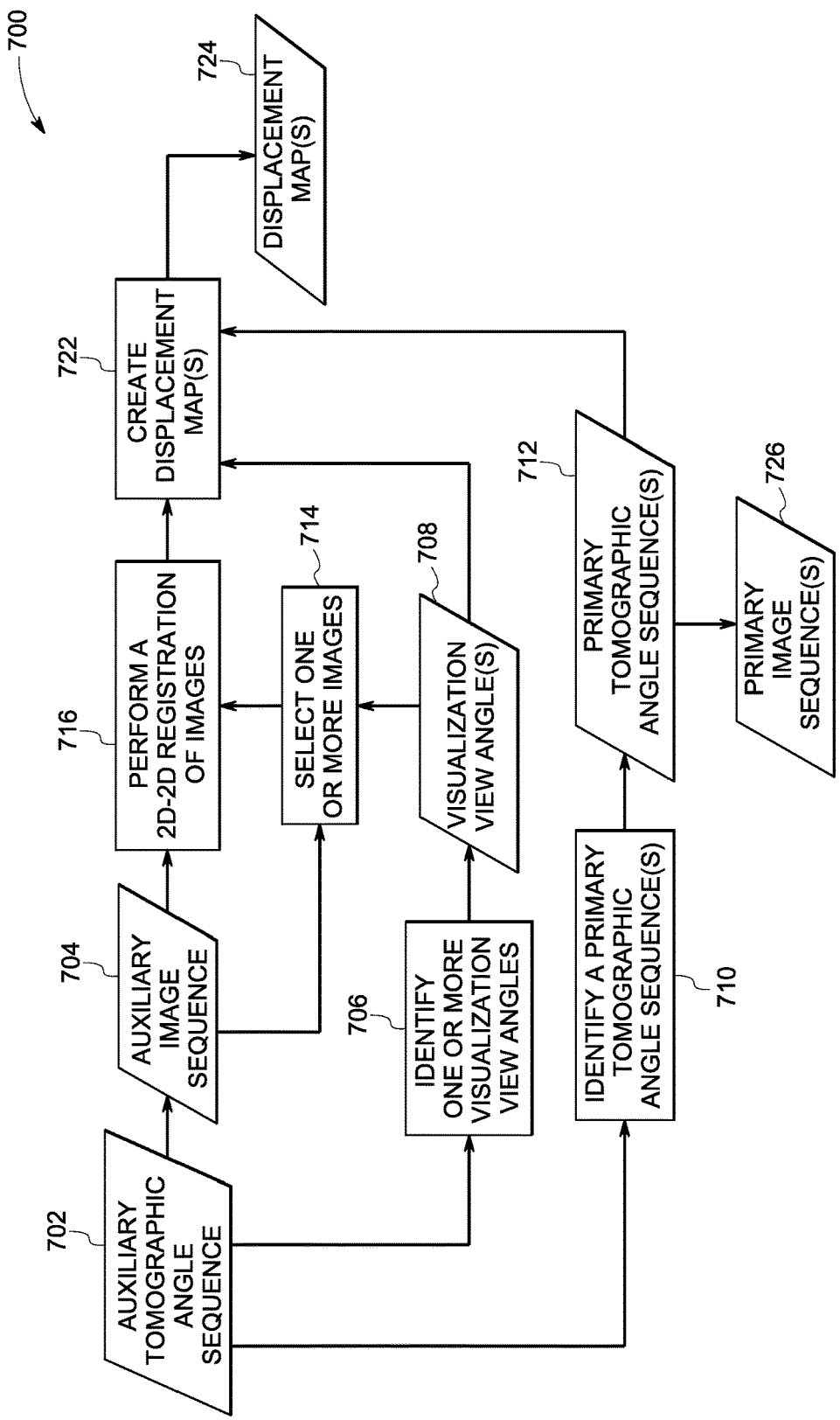
FIG. 7 is a flow chart depicting another method for generating a displacement map, in accordance with aspects of the present specification.

FIGS. 6-7 are flow charts 600, 700 that depict step 408 of FIG. 4 in greater detail. In particular, FIGS. 6-7 depict a set of alternative methods for creating displacement maps. The displacement maps may then be used to transform or warp images in an image sequence such that the warped images in a stabilized image sequence appear as images corresponding to a given static visualization view angle. The methods of FIGS. 6-7 are described with reference to the elements of FIGS. 1-5.

Referring now to FIG. 6, a flow chart 600 depicting a method for determining geometric information and deriving displacement map(s) based on the determined geometric information and a selected visualization view angle is presented. In particular, FIG. 6 presents a method for deriving 2D-2D correspondences and the associated displacement maps using a 3D model of a structure of interest. The method of FIG. 6 entails deriving geometric information such as 3D locations corresponding to one or more structures of interest from projection images in one auxiliary image sequence 604 that corresponds to an auxiliary tomographic angle sequence 602. The geometric information may then be used in conjunction with pre-defined visualization view angles 622 and a primary tomographic angle sequence 618 corresponding to a primary projection image sequence 620 to generate one or more displacement maps.

In one embodiment, a 3D representation or 3D model of the structure of interest may be established by using a reconstruction of a volumetric image based on the auxiliary image sequence 604 or a subset thereof. Subsequently, the structures of interest may be extracted from this volumetric image. In another embodiment, the structures of interest may be identified and segmented in the 2D projection images such as the auxiliary image sequence 604 or a subset thereof, followed by a reconstruction of the 3D positions of the structures. In certain embodiments, a triangulation process may be employed to reconstruct the 3D model.

By way of example, an image sequence corresponding to a tomographic angle sequence may be acquired. This image sequence may be generally referred to as an auxiliary image sequence 604 and the corresponding tomographic angle sequence may be referred to as an auxiliary tomographic angle sequence 602. It may be noted that images in the auxiliary image sequence 604 may include one or more structures of interest and may thus be used to determine the 3D locations of one or more structures of interest.

To that end, at step 606, one or more structures of interest in the images in the auxiliary image sequence 604 may be extracted. The structures of interest may include a guide wire, a needle, opacified vasculature, and the like. The structures of interest may be extracted via use of segmentation techniques, such as, but not limited to, thresholding or other known techniques. In certain other embodiments, edges, contours, centerlines, and the like of the structures of interest may be extracted from the images. Additionally, subtraction imaging may be used in conjunction with segmentation techniques for facilitating the extraction/segmentation of the structures of interest. By way of example, projection images corresponding to one tomosynthesis orbit may be acquired without use of injected contrast. Subsequently, using the same trajectory as the previous orbit another set of projection images may be acquired with use of injected contrast. Images in one set of projection images may be subtracted from corresponding images in the other set of projection images to obtain images containing only the opacified vasculature, while suppressing all other image content through the subtraction.

Subsequently, at step 608, a 3D reconstruction of 3D positions of the structures of interest from the structures of interest extracted from the 2D images (step 606) may be performed to create a 3D model. In one embodiment, a triangulation process may be used to identify locations of the segmented structures of interest in a 3D domain. It may be noted that generally a reconstruction of a 3D volume from projection data requires knowledge of the imaging geometry. This known geometry is generally represented by the auxiliary tomographic angle sequence 602 and may be used directly to compute the 3D position of structures that were identified in the projection images (without having to reconstruct a full 3D volume). Once the 3D positions of the extracted structures of interest are determined, the 3D model may be generated based on the 3D positions of the one or more structures of interest.

Alternatively, as depicted in step 612, 3D locations may be determined by first reconstructing a 3D image volume based on the images in the auxiliary image sequence 604. This step is based on the collected projection images and the known imaging geometry (represented by the tomographic angle sequence) and may be performed by using a tomosynthesis reconstruction algorithm. Subsequently, at step 614, one or more structures of interest may be extracted from the 3D image volume to determine the 3D locations of the structures of interest. The structures of interest may be extracted by applying thresholding or other segmentation techniques to the reconstructed tomosynthesis volume. In one embodiment, the reconstruction is based on subtracted projection images. As a result of the processing of steps 606-608 or 610-612, 3D locations of the structures of interest may be established. The 3D locations of points located in the 3D volume are representative of the location of the structure of interest. In one example, the 3D locations of the structures of interest may be generally referred to as geometric information 610.

Based on a primary tomographic angle sequence 618, another image sequence 620 may be acquired. This other image sequence may generally be referred to as a primary image sequence 620. In the present example, the primary image sequence 620 is different from the auxiliary image sequence 604. Also, the primary tomographic angle sequence 618 may be different from the auxiliary tomographic angle sequence 602. In another example, the primary and auxiliary tomographic angle sequences 618, 602 may be the same, but the primary and auxiliary image sequences 604, 620 may be different (e.g., due to the fact that these image sequences are acquired at different times for a repeat orbit traversing the same trajectory). In yet another example, both the tomographic angle sequences 618, 602 and the image sequences 620, 604 may be the same.

Once the geometric information 610 such as the 3D locations of the structures of interest are determined, displacement maps 624 may be created, as depicted by step 616. As previously noted, displacement maps may be representative of mappings that include a set of correspondences between the locations of one or more points in a 3D structure in two different projection images that correspond to two different view angles. Specifically, the 3D model may be forward projected for two different projection angles that correspond to the two projection images. The term "forward projecting" is used to refer to the process of computing the location of a 3D point in a projection image, based on the known 3D location of the point and the known imaging geometry (or projection geometry). These forward projected 3D locations define locations of corresponding points in different projection images. In one example, one of the view angles may correspond to the view angle associated with an acquired projection image (for example, one angle in the primary tomographic angle sequence 618), while the other view angle may correspond to a pre-defined visualization view angle such as the visualization view angle 622. These locations establish a 2D-2D correspondence and may therefore be used to determine a displacement map 624. This displacement map 624 may be used to warp a projection image from the primary image sequence 620 associated with a view angle from the primary tomographic angle sequence 618 such that the structures of interest in the warped image appear as being viewed from the visualization view angle 622. It may be noted that the visualization view angle may be outside of the tomosynthesis orbit, that is, the visualization view angle may not necessarily correspond to a view angle at which projection data was actually acquired.

At step 616, the displacement maps 624 may be generated based on user-specified visualization view angles 622, the primary tomographic angle sequence 618, and the geometric information. Consequent to the processing of step 616, one or more displacement maps 624 may be created. The displacement maps 624 may be used to warp images in a primary image sequence 620 to generate a stabilized image sequence (see step 418 of FIG. 4). As previously noted, the stabilized image sequence is representative of an image sequence where structures of interest in the stabilized images appear static with respect to a pre-defined view angle.

The example of deriving displacement maps 624 using a 3D model (as illustrated in FIG. 6) facilitates mapping of acquired projection images to visualization view angles that may differ from any subset of the tomographic projection angle sequence since corresponding points in these projection images may be determined based on the 3D model and a selected arbitrary projection geometry (that is, for any selected visualization view angle). Consequently, warped images corresponding to visualization view angles that lie outside of the current acquisition trajectory may be generated. The stabilized image sequence may be visualized on a display (see step 420 of FIG. 4).

It may be noted that the same set of 3D locations (as generally represented by the geometric information 610) may be used to map different projection sequences to the same view angles. For example, a sequence of images acquired with an opacified vascular tree may be used to both create a 3D structure of the vascular tree as well as create a stabilized image sequence visualizing the stabilized opacified vascular tree. Subsequently, a projection image sequence of a catheter only (without contrast bolus) may be acquired with a different trajectory (that is, angles may be different for different sequences). In one example, the catheter image sequence may be acquired with a smaller tomographic angle. Using the 3D locations derived from the vascular sequence together with the projection angles from the catheter sequence and the visualization view angles, a stabilized catheter image sequence may be created from the acquired catheter image sequence. Stabilized image sequences for the same visualization view angle may be displayed in a superimposed, side-by-side, or similar configurations. For example, stabilized images corresponding to the vasculature may be superimposed on the stabilized image sequence corresponding to the interventional devices, thereby facilitating visualization of spatial relationships between device(s) and anatomy. In certain other embodiments, the images representative of the vasculature and/or interventional device (where at least one of the sequences is a stabilized image sequence) may be displayed alongside each other.

In this example, the auxiliary tomographic angle sequence 602 may correspond to an acquisition of a contrast injected vascular tree, which is used to derive the geometric information. The primary tomographic angle sequence 618 may correspond to an acquisition, where a catheter is visible in the images, without contrast bolus injection. Associated displacement maps may be employed to warp the primary image sequence 620, thereby providing one or more stabilized image sequences that aid in visualizing the catheter. Furthermore, a similar stabilization may be applied to the auxiliary image sequence 602 relative to the same visualization view angle, to visualize the stabilized vascular tree. In this manner, the location of the catheter with respect to the vascular structure and/or the location of the vascular tree may be visualized on a display. This display shows the spatial relationship between catheter and vascular tree and aids a clinician in the evaluation of the images, although the catheter image is acquired without contrast, that is, the vascular tree in the "catheter images" is not visible. The stabilized image sequences generated in that manner may be displayed side-by-side, or they may be displayed as an overlay, etc., to further facilitate interpretation of the images. In addition, stabilized image sequences may be generated for two or more visualization view angles, thereby further aiding in the interpretation of the 3D structure/shape of the imaged devices and the anatomy. Furthermore, the displayed image showing the anatomy (in this example, the vessel tree) may be an averaged (over time) stabilized image sequence, a projection image, a rendering of a reconstructed volume, a cross-section (for example, a planar reformat) of a 3D volumetric reconstruction and the like, and will be discussed in greater detail hereinafter.

Turning now to FIG. 7, a flow chart 700 depicting an alternative method for determining geometric information and deriving displacement map(s) based on the determined geometric information is presented. In the method of FIG. 7, a 2D-2D correspondence between locations of structures of interest in images in a projection image sequence may be derived by performing a 2D-2D non-rigid registration. This process brings the structures of interest in the projection images into alignment, thereby establishing a 2D-2D correspondence and a mapping between points in pairs of projection images. Associated displacement maps may be derived based on the 2D-2D correspondence. The displacement maps may be used to deform/warp one or more images in an image sequence such that structures of interest in the one or more warped images appear as being viewed from a different visualization view angle. In this example, displacement maps may be derived corresponding to tomographic projection angles for which image data is acquired. Accordingly, in this example, the one or more visualization view angles may be selected from the set of angles corresponding to the auxiliary tomographic angle sequence. In addition, the primary tomographic angle sequence may be selected as a subset of the auxiliary tomographic angle sequence.

Accordingly, in the example of FIG. 7, one or more visualization view angles 708 may be identified, as depicted by step 706. In this example, the visualization view angles 706 may correspond to a subset of angles of an auxiliary tomographic angle sequence 702. In addition, an auxiliary image sequence 704 corresponding to the auxiliary tomographic angle sequence 702 may be acquired. The auxiliary image sequence 704 may be used to create one or more displacement maps.

Further, at step 714, one or more projection images may be selected from the auxiliary image sequence 704. Specifically, the selected projection images have associated tomographic angles that correspond to the identified visualization view angles 708. At step 716, a 2D-2D non-rigid registration may be performed using pairs of images in the auxiliary image sequence 704 and images selected at step 714 to generate geometric information. The 2D-2D non-rigid registration between the pairs of projection images aids in establishing a mapping between corresponding points in the pairs of projection images. In particular, by registering an image from the auxiliary image sequence 704 to an image corresponding to a visualization view angle (that is, an image selected at step 714), a mapping is established. This mapping may be used to warp the image from auxiliary image sequence 704 such that the structures of interest in the warped image appear as being viewed from the visualization view angle 708.

Moreover, at step 710, another sequence of tomographic angles 712 may be identified. This sequence of tomographic angles may be referred to as a primary tomographic angle sequence 712. In this example, the primary tomographic angle sequence 712 corresponds to a subset of the sequence of tomographic angles associated with the auxiliary tomographic angle sequence 702. Subsequently, at step 722, the primary tomographic angle sequence 712 may be used to create the associated displacement maps. Specifically, at step 722, one or more displacement maps 724 may be created based on identified visualization view angles 708, the primary tomographic angle sequence 712, and the geometric information such as mapping/correspondence established consequent to the processing of step 716.

Also, an image sequence that corresponds to the primary tomographic angle sequence 712 may be referred to as a primary image sequence 726. The displacement maps 724 created at step 722 may be used to warp an image in the primary image sequence 726 such that the structures of interest in the warped image appear as being viewed from the visualization view angle 708. In the example of FIG. 7, the primary image sequence 726 may be the same as the auxiliary image sequence 704 or a subset thereof. The primary image sequence may also be a different image sequence, where the associated primary tomographic angle sequence may be the same as the auxiliary tomographic angle sequence, or a subset thereof. In another example, two or more primary image sequences may be processed to generate stabilized image sequences using the appropriate displacement maps, where the tomographic angle sequence associated with each of the primary image sequences is a subset of the auxiliary tomographic angle sequence.

In certain embodiments, the 2D-2D non-rigid registration may be performed in an iterative manner. By way of example, at the outset, pairs of images that are adjacently disposed in the auxiliary image sequence 704 or pairs of images that are disposed close to one another (for example, where the associated view angles are close to one another) may be processed via the 2D-2D non-rigid registration to establish correspondence/mappings between associated points in the images. Subsequently, the mappings may be chained together to establish a correspondence for points in projection images that are located farther apart in the auxiliary image sequence 704.

With returning reference to FIG. 5, it may be appreciated while the vascular tree 506 depicted in FIG. 5 is shown without any superimpositions of vessels or branches of the vasculature in the projection images, in certain situations such ambiguities (for example, vessels that cross in one, or even both, projection images) may arise. In accordance with further aspects of the present specification, the method may also aid in addressing any ambiguities in registration points in the structure of interest. Different strategies may be used in addressing ambiguities, depending on whether the ambiguities arise in a projection image associated with an acquired projection image or whether they arise in an image as seen from a visualization view angle.

In the event that the ambiguities arise in the image of the entire structure of interest when seen from a visualization view angle, the ambiguities may be addressed by narrowing the region of interest to a subset, or "currently most relevant part," of the structure of interest. In accordance with aspects of the present specification, ambiguities in the registration points may be resolved by identifying a region around a catheter tip. The selection of the region around the catheter tip aids in identifying a region of interest (ROI) within the vascular tree, and differentiating this region from other (potentially superimposed) sections of the vasculature. Displacement maps may now be generated such that in the region around the catheter tip, for example, the displacement map addresses the displacement/correspondence of the section of the vasculature associated with the current location of the catheter tip, and not associated with any superimposed branches of the vasculature.

In some embodiments, the identification of the ROI (for example, the catheter tip location) may entail user assistance or may be automated. In addition, in one embodiment, the catheter or other interventional devices may be tracked through the 3D image volume to allow identification of the tip of the advancing or retracting catheter/interventional device. Techniques such as differential processing may be used to track the advancing/retracting catheter/interventional device. By way of example, a difference image between a current image and one or more prior images in the image sequence may be generated. This type of approach may be used to address potential ambiguities.

In the event that the ambiguities arise in one or more projection views of the entire structure of interest that are acquired as part of the primary image sequence (that is, a subset of the images that are to be warped in order to create a stabilized image sequence), the ambiguities may be addressed, by circumventing regions with ambiguities when processing the image sequence. Information corresponding to the regions with ambiguities may be "left out." Any missing information in the resulting stabilized image sequence corresponding to the regions with ambiguities may be obtained via use of adjacent images/views in the image sequence. By way of example, a region with ambiguities may include a segment of vasculature. This segment of vasculature may not be processed for a determined portion of the scan that includes overlapping structures. During this part of the scan, the corresponding region(s) in the stabilized image sequence may be filled in by using information from adjacent views in the stabilized image sequence. In one embodiment, the missing information may be filled in in conjunction with a temporal average. In this example, the image sequence that is displayed for use by the clinician may include a temporal average. One example of the temporal average may include a weighted average of the past N stabilized views, with a highest weight generally being assigned to the most recent stabilized image. Locations with ambiguities may be "left out" of the averaging process, that is, at each location within the image, information from warped images without ambiguities with appropriate averaging (where in the averaging process data that was left out is appropriately accounted for) may be used.

In one embodiment, the temporal averaging may be used (for example, in combination with appropriate high-pass filtering or other processing steps, where these steps may be adapted to the current imaging geometry and tomographic trajectory) to further suppress background in the stabilized image sequences. More specifically, since the structures of interest are stabilized in the image, there is no change in the corresponding locations in the stabilized images, and temporal averaging does not lead to a spatial blurring of the structures of interest. For other structures in the images, however, the location in the stabilized images changes as a function of the primary view angle, and temporal averaging may lead to a spatial blurring of those structures, thereby resulting in a further improved visibility of the structures of interest within the image. It may be noted that the amount of temporal blurring/averaging may be adapted to the region of interest. For example, for navigating a catheter, the amount of temporal averaging near the tip of the catheter may be kept small so as not to blur the tip of the catheter.

In accordance with further aspects of the present specification, an injected contrast bolus may be used to opacify the vasculature. A corresponding image sequence may be used to extract 3D information about the vascular tree. In one embodiment, this acquisition may be associated with a relatively large tomographic angle (for example, +/−30 degrees). Consequently, an enhanced 3D resolution of the 3D vasculature and/or surrounding anatomical detail may be achieved. Also, a 3D rendering of the vascular tree may be generated such that two or more view angles may be selected for optimal viewing. This rendering may be based on a reconstructed 3D volume, where the 3D volume may be reconstructed based on the acquired projection images by using a tomosynthesis reconstruction algorithm. Alternatively, the rendering may be based on a reconstructed 3D structure of the vasculature, which in turn may be based on the segmented vasculature in the projection images from which the 3D structure of the vasculature is derived.

From the image sequence corresponding to the vascular tree (vascular image sequence) displacement maps may be derived and used to stabilize the image sequence such that the vascular image sequence is shown from the selected view angles. Furthermore, as the catheter is advanced through the vasculature, corresponding images may be acquired. These images may be generally referred to as a catheter image sequence. The displacement maps derived from the vascular image sequence may be used to create a stabilized catheter image sequence. More specifically, geometric information may be transferred from one dataset to another. Since it may be desirable to reduce the need for iodinated contrast, previously acquired image(s) of contrast filled vasculature may be overlaid over the current image(s) to assist the user in guiding the catheter without the need for an additional iodine contrast bolus. In this example, for navigating the catheter within the vasculature, the displacement map derived from the vasculature may be applied to the catheter image. The underlying assumption is that the catheter occupies the same spatial "footprint" as the vascular tree, and that the derived displacement maps are derived for corresponding projection view angles and visualization view angles.

In one embodiment, the catheter image sequence may be acquired using a smaller tomographic angle than the tomographic angle used for the acquisition of the vascular image sequence. Since the view angles used for this image sequence are different from those corresponding to the vascular image sequence, geometric information corresponding to the catheter image sequence may be generated based on the associated angle sequence, the 3D structure of the vasculature, and the selected view angles. In this example, displacement information/maps corresponding to the catheter image sequence may be used to stabilize the catheter images instead of the displacement maps derived from the vasculature.

Various combinations of images may be displayed on a display and presented to the clinician. For example, the vascular structure corresponding to the selected view angles may be displayed as one or more of a projection image corresponding to that angle, a stabilized image, a stabilized image with temporal averaging, a rendering of a reconstructed 3D volume or the 3D structure, an appropriate cross-section (for example, planar reformat) through the reconstructed volume, and the like. A stabilized image sequence of the advancing catheter may be visualized by superimposing the stabilized image sequence over the displayed vascular image, or otherwise in a well-defined and easy to interpret spatial relationship to the vascular images.

Moreover, in certain situations, periodically, small amounts of contrast may be injected in order to update the image(s) of the vascular tree; to update the geometric information, to detect mis-registration, and the like. For these image sequences, a larger tomographic angle may be used. Further, as the intervention progresses, additional visualization view angles may be selected or visualization view angles may be adapted, and the previously collected image sequences, as well as currently acquired image sequences may be processed to provide stabilized image sequences for the new/updated view angle(s).

Furthermore, the acquisition trajectory, view angles, and corresponding update rates may be adapted in real-time. In particular, gantry trajectory, view angles, and other imaging and processing parameters may be adapted in real-time or near real-time based on the local geometry. Moreover, the tomographic angle may also be adapted.

In addition, the catheter image sequence may be stabilized using displacement map(s) derived from the vascular image sequence. These displacement maps may be pre-computed since the displacement maps are based on a previously acquired image sequence. In one embodiment, the 2D projection images may be warped in real-time or near real-time. By way of example, the images may be warped in real-time or near real-time for use in multi-perspective visualization of an advancing catheter/guide wire to support navigation of the catheter/guide wire in the vasculature of the patient. Furthermore, the displacement maps aid in providing a real-time display of the stabilized image sequence. Stabilized images in the stabilized catheter image sequence that include the catheter may be displayed to the clinician. In one example, the stabilized catheter image sequence may be superimposed on the images showing the opacified vascular tree. Alternatively, the stabilized image sequence may be displayed alongside or in any other arrangement, thereby allowing the clinician to evaluate the position of the catheter relative to the vasculature. In one embodiment, the superimposition of the stabilized catheter image sequence on the vascular image sequence may be used to detect any mis-registration in the images. The mis-registration may be a result of patient motion and the like. In such a situation, an additional contrast bolus may be injected, and a new vascular image sequence may be acquired.

Although the system and method presented hereinabove are described with reference to application in multi-perspective imaging for catheter navigation using a single-plane imaging system, use of the present system and method in other applications such as quantification of vessel diameter, needle and device placement in oncology, and the like is envisaged. The method may also be used in conjunction with a bi-plane imaging system.

In addition, the foregoing examples, demonstrations, and process steps such as those that may be performed by the system may be implemented by suitable code on a processor-based system, such as a general-purpose or special-purpose computer. It should also be noted that different implementations of the present specification may perform some or all of the steps described herein in different orders or substantially concurrently, that is, in parallel. Furthermore, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

It may be noted that the foregoing examples, demonstrations, and process steps that may be performed by certain components of the present systems, for example by the system 100, the processing components 130, the system controller 122, and the multi-perspective imaging platform 144 of FIG. 1, may be implemented by suitable code on a processor-based system. To that end, the processor-based system, for example, may include a general-purpose or a special-purpose computer. It may also be noted that different implementations of the present specification may perform some or all of the steps described herein in different orders or substantially concurrently.

Although specific features of various embodiments of the present specification may be shown in and/or described with respect to some drawings and not in others, this is for convenience only. It is to be understood that the described features, structures, and/or characteristics may be combined and/or used interchangeably in any suitable manner in various embodiments.

The systems and methods described hereinabove provide a framework that advantageously provides multi-perspective imaging capability using a single-plane imaging system, thereby eliminating the need for multi-plane imaging systems and simplifying workflow. Furthermore, the systems and methods presented herein provide image stabilization. In addition, the systems and methods also provide 3D information/context while circumventing the need for performing a full-fledged 3D reconstruction. Also, the systems and methods are non-intrusive and the continuous trajectory enables acquisition of a temporal series of 3D information.

Additionally, the systems and methods of the present specification aid in displaying projection images from one or more view angles or other user-specified perspectives from a single-plane interventional X-ray system. Moreover, geometric information derived from one image sequence is used to perform stabilization of one or more image sequences, where structures of interest in the stabilized image sequence appear static with respect to a pre-defined view angle. Furthermore, a display of stabilized image set(s) which includes a set of images representing a 3D structure as seen from two (or more) static view angles at a point in time provides the user an "easy to read" visualization. Also, images corresponding to the vasculature and/or interventional devices may be superimposed on the stabilized image sequences, thereby providing visualization of anatomical relationship. In addition, the multi-perspective display of the image sequences facilitates enhanced visualization of the imaged volume, thereby providing visualization support to the user for diagnosis and guidance support during interventional procedures.

The display of the stabilized image sequences corresponding to two or more view angles and/or other sequences such as the vascular image sequence and the catheter image sequence enhances the visual support to the user. For example, the multi-perspective visualization provided by the stabilized image sequences facilitates faster and easier navigation of catheters. Moreover, the systems and methods provide a flexible choice of visualization view angles/perspectives that are not constrained to lie on the acquisition trajectory. Additionally, the choice of the visualization view angles circumvents any modification to the gantry trajectory. Furthermore, use of the systems and methods presented hereinabove aids in facilitating limited angle 3D imaging with minimal impact on workflow.

As will be appreciated, in such tomosynthesis acquisitions, an acquisition motion or trajectory having a small tomographic angle may be employed. Such an embodiment allows a user easy access to a patient, while circumventing collision hazards with procedure room apparatus, patient, and/or other medical staff, thereby overcoming shortcomings of the currently available techniques.

While only certain features of the disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A method for imaging a target region in a subject, the method comprising:
   selecting, via a multi-perspective imaging platform, one or more tomographic angle sequences;
   acquiring, via a single-plane imaging system, one or more image sequences corresponding to the one or more tomographic angle sequences, wherein each of the one or more image sequences has a corresponding tomographic angle sequence;
   deriving, via the multi-perspective imaging platform, geometric information corresponding to one or more structures of interest in at least one of the one or more image sequences;
   identifying, via the multi-perspective imaging platform, visualization information;
   generating, via the multi-perspective imaging platform, one or more displacement maps based on the geometric information, the visualization information, at least a subset of at least one of the one or more tomographic angle sequences, or combinations thereof, wherein generating the one or more displacement maps comprises determining a mapping based on the geometric information corresponding to the one or more structures of interest, the visualization information, at least the subset of at least one of the one or more tomographic angle sequences, or combinations thereof;

transforming, via the multi-perspective imaging platform, at least a subset of images in the one or more image sequences based on corresponding displacement maps to create one or more transformed/stabilized image sequences, wherein transforming at least the subset of images comprises warping at least the subset of images based on a corresponding displacement map to generate the one or more transformed/stabilized image sequences; and visualizing, via the multi-perspective imaging platform, on a display the one or more transformed/stabilized image sequences to provide a stabilized presentation of the target region.

2. The method of claim 1, wherein selecting the one or more tomographic angle sequences comprises identifying at least one tomographic angle sequence such that the tomographic angle sequence facilitates acquisition of at least one image sequence, wherein a source of the imaging system is configured to move about a first side of the target region and a detector of the imaging system is configured to move about a second side of the target region, and wherein the second side is opposite the first side.

3. The method of claim 1, wherein the visualization information comprises one or more visualization view angles.

4. The method of claim 3, further comprising transforming at least a subset of images in the one or more image sequences to provide a stabilized presentation of the target region for each of the one or more visualization view angles.

5. The method of claim 3, wherein identifying the visualization information comprises selecting two or more visualization view angles, and wherein the two or more visualization view angles are separated by at least 45 degrees.

6. The method of claim 3, wherein identifying the visualization information comprises selecting at least one visualization view angle from a tomographic angle sequence corresponding to an acquisition trajectory of the one or more image sequences.

7. The method of claim 3, wherein identifying the visualization information comprises selecting at least one visualization view angle that lies outside an acquisition trajectory of the one or more image sequences.

8. The method of claim 1, wherein at least one image sequence in the one or more image sequences is identified as a primary image sequence corresponding to a primary tomographic angle sequence, and wherein at least one image sequence in the one or more image sequences is identified as an auxiliary image sequence corresponding to an auxiliary sequence of tomographic angles.

9. The method of claim 8, wherein the primary image sequence is different from the auxiliary image sequence.

10. The method of claim 8, wherein deriving the geometric information comprises determining three-dimensional locations of the one or more structures of interest from the auxiliary image sequence.

11. The method of claim 10, wherein determining the mapping comprises determining the mapping based on the three-dimensional locations of the one or more structures of interest, the primary tomographic angle sequence, the visualization information, or combinations thereof.

12. The method of claim 11, wherein the mapping comprises correspondences between locations of the one or more structures of interest in corresponding images in the primary image sequence and in forward projected three-dimensional locations of the one or more structures of interest corresponding to at least one of one or more visualization view angles.

13. The method of claim 8, wherein deriving the geometric information comprises performing a non-rigid registration of pairs of projection images in the auxiliary image sequence to create a mapping between the locations of corresponding points in different projection images.

14. The method of claim 1, wherein structures of interest in the one or more stabilized image sequences appear static with respect to a visualization view angle.

15. The method of claim 14, wherein transforming the images in at least the subset of images further comprises temporal averaging of the images, filtering of the images, or a combination thereof.

16. The method of claim 1, wherein visualizing comprises one or more of a superimposed display, a side-by-side display, a toggled display, or combinations thereof.

17. The method of claim 16, wherein visualizing further comprises generating a simultaneous display of the one or more stabilized image sequences corresponding to an interventional device, and one or more images or image sequences corresponding to anatomical context by organizing the one or more stabilized image sequences corresponding to the interventional device and the one or more images or image sequences corresponding to the anatomical context in a determined spatial relationship.

18. The method of claim 1, wherein transforming at least the subset of images and the visualizing are performed in real-time or near real-time.

19. The method of claim 1, further comprising adapting in real-time or near real-time a tomographic angle, an acquisition trajectory, the visualization information, or combinations thereof based on a local geometry of the target region.

20. A system, comprising:
a multi-perspective imaging platform, configured to:
select one or more tomographic angle sequences;
acquire one or more image sequences corresponding to the one or more tomographic angle sequences, wherein each of the one or more image sequences has a corresponding tomographic angle sequence;
derive geometric information corresponding to one or more structures of interest in at least one of the one or more image sequences;
identify visualization information;
generate one or more displacement maps based on the geometric information, the visualization information, at least a subset of at least one of the one or more tomographic angle sequences, or combinations thereof, wherein to generate the one or more displacement maps the multi-perspective imaging platform is configured to determine a mapping based on the geometric information corresponding to the one or more structures of interest, at least the subset of at least one of the one or more tomographic angle sequences, or combinations thereof;
transform at least a subset of images in the one or more image sequences based on corresponding displacement maps to create one or more transformed/stabilized image sequences, wherein to transform at least the subset of images the multi-perspective imaging platform is configured to warp at least the subset of images based on a corresponding displacement map to generate the one or more transformed/stabilized image sequences; and
visualize on a display the one or more transformed/stabilized image sequences to provide a stabilized presentation of the target region.

21. A system for imaging a target region in a subject, the system comprising:

an acquisition unit configured to obtain one or more image sequences corresponding to a target region in a subject;
a processing unit in operative association with the acquisition unit and comprising a multi-perspective imaging platform, wherein the multi-perspective imaging platform is configured to:
select one or more tomographic angle sequences;
acquire one or more image sequences corresponding to the one or more tomographic angle sequences, wherein each of the one or more image sequences has a corresponding tomographic angle sequence;
derive geometric information corresponding to one or more structures of interest in at least one of the one or more image sequences;
identify visualization information;
generate one or more displacement maps based on the geometric information, the visualization information, at least a subset of at least one of the one or more tomographic angle sequences, or combinations thereof, wherein to generate the one or more displacement maps the multi-perspective imaging platform is configured to determine a mapping based on the geometric information corresponding to the one or more structures of interest, at least the subset of at least one of the one or more tomographic angle sequences, or combinations thereof;
transform at least a subset of images in the one or more image sequences based on corresponding displacement maps to create one or more transformed/stabilized image sequences, wherein to transform at least the subset of images the multi-perspective imaging platform is configured to warp at least the subset of images based on a corresponding displacement map to generate the one or more transformed/stabilized image sequences; and
visualize on a display the one or more transformed/stabilized image sequences to provide a stabilized presentation of the target region.

22. The system of claim 21, wherein the system is an X-ray imaging system.

* * * * *